(12) United States Patent
Gronau et al.

(10) Patent No.: US 9,808,566 B2
(45) Date of Patent: Nov. 7, 2017

(54) EXTERNAL FUNCTIONAL MEANS, BLOOD TREATMENT APPARATUS FOR RECEIVING AN EXTERNAL FUNCTIONAL MEANS IN ACCORDANCE WITH THE INVENTION, AND METHOD

(75) Inventors: Soeren Gronau, Nauheim (DE); Goetz Guenther, Oberursel (DE); Juergen Haecker, Neu-Anspach (DE); Martin Lauer, St. Wendel (DE); Joachim Manke, Loehnberg (DE); Dejan Nikolic, Frankfurt (DE); Manfred Weis, St. Wendel (DE); Andrea Günther, legal representative, Oberursel (DE); Richard Robert Bernd Günther, legal representative, Stuttgart (DE); Gesa Dagmar Günther, legal representative, Stuttgart (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1007 days.

(21) Appl. No.: 12/766,424

(22) Filed: Apr. 23, 2010

(65) Prior Publication Data

US 2010/0274168 A1     Oct. 28, 2010

Related U.S. Application Data

(60) Provisional application No. 61/185,643, filed on Jun. 10, 2009.

(30) Foreign Application Priority Data

Apr. 23, 2009   (DE) ......................... 10 2009 018 664
Jun. 10, 2009   (DE) ......................... 10 2009 024 468

(51) Int. Cl.
*A61M 1/14*    (2006.01)
*A61M 1/36*    (2006.01)
(Continued)

(52) U.S. Cl.
CPC ............ *A61M 1/3621* (2013.01); *A61M 1/30* (2013.01); *A61M 1/303* (2014.02);
(Continued)

(58) Field of Classification Search
USPC ........................................................ 604/5.04
See application file for complete search history.

(56) References Cited

U.S. PATENT DOCUMENTS 4,436,620 A * 3/1984 Bellotti ............... A61M 1/3621
                                                  210/321.8
4,479,762 A * 10/1984 Bilstad ................ A61M 1/3496
                                                      206/364

(Continued)

FOREIGN PATENT DOCUMENTS

DE        19837667 A1    3/2000
DE     102009036101.4 A1    2/2001
(Continued)

OTHER PUBLICATIONS

PCT International Search Report from PCT/EP2010/002488, mailed on Sep. 30, 2010.
(Continued)

*Primary Examiner* — Todd J Scherbel
*Assistant Examiner* — Guy K Townsend
(74) *Attorney, Agent, or Firm* — Fish & Richardson P.C.

(57) ABSTRACT

An external functional means comprises at least one housing body, at least one chamber integrated into the housing body for receiving medical fluids, at least one passage integrated into the housing body for receiving and/or conducting a medical fluid, and at least one valve means completely or partly integrated into the housing body for controlling or regulating a fluid flowing through the external functional means. The invention further specifies a blood treatment apparatus and methods which may be carried out by means (Continued)

of the external functional means of the invention and by means of the blood treatment apparatus, respectively.

60 Claims, 20 Drawing Sheets

(51) Int. Cl.
*A61M 1/30* (2006.01)
*A61M 39/10* (2006.01)
*B29L 31/00* (2006.01)
*B29C 65/16* (2006.01)
*B29C 65/00* (2006.01)

(52) U.S. Cl.
CPC .............. *A61M 2039/1094* (2013.01); *A61M 2205/123* (2013.01); *A61M 2205/128* (2013.01); *A61M 2205/273* (2013.01); *B29C 65/16* (2013.01); *B29C 66/53461* (2013.01); *B29L 2031/753* (2013.01)

(56) References Cited

U.S. PATENT DOCUMENTS

| | | | |
|---|---|---|---|
| 4,666,598 A | 5/1987 | Heath et al. | |
| 4,770,769 A * | 9/1988 | Schael | A61M 1/16 210/104 |
| 5,470,483 A * | 11/1995 | Bene | A61M 1/3441 210/130 |
| 5,628,908 A * | 5/1997 | Kamen | A61M 1/28 210/180 |
| 5,783,072 A * | 7/1998 | Kenley | A61L 2/04 210/195.2 |
| 6,132,616 A * | 10/2000 | Twardowski | A61M 1/3643 210/645 |
| 6,471,855 B1 * | 10/2002 | Odak | A61M 1/3693 210/134 |
| 6,542,761 B1 * | 4/2003 | Jahn | A61M 1/3639 600/310 |
| 6,645,166 B2 * | 11/2003 | Scheunert | A61M 1/30 210/645 |
| 6,695,803 B1 * | 2/2004 | Robinson | A61M 1/02 210/252 |
| 6,752,172 B2 * | 6/2004 | Lauer | A61M 1/367 137/605 |
| 7,195,607 B2 * | 3/2007 | Westberg | A61M 1/1037 210/258 |
| 7,488,301 B2 * | 2/2009 | Beden | A61M 1/16 210/645 |
| 7,648,627 B2 * | 1/2010 | Beden | A61M 1/1037 210/321.6 |
| 7,935,074 B2 * | 5/2011 | Plahey | A61M 1/28 210/646 |
| 8,142,653 B2 * | 3/2012 | Beden | A61M 1/1037 210/240 |
| 2002/0062109 A1 * | 5/2002 | Lauer | A61M 1/367 604/256 |
| 2003/0042181 A1 * | 3/2003 | Metzner | A61M 1/3639 210/85 |
| 2003/0130607 A1 | 7/2003 | Delnevo et al. | |
| 2003/0220607 A1 * | 11/2003 | Busby | A61M 1/28 604/29 |
| 2004/0084647 A1 * | 5/2004 | Beden | A61M 1/367 251/61.1 |
| 2004/0186416 A1 | 9/2004 | Caleffi | |
| 2005/0017505 A1 * | 1/2005 | Thilly | A61M 39/18 285/45 |
| 2005/0045548 A1 | 3/2005 | Brugger et al. | |
| 2005/0230292 A1 * | 10/2005 | Beden | A61M 1/1037 210/85 |
| 2005/0283132 A1 * | 12/2005 | Stanus | A61J 1/1475 604/403 |
| 2006/0079826 A1 * | 4/2006 | Beden | A61M 1/16 604/4.01 |
| 2006/0155236 A1 | 7/2006 | Gara et al. | |
| 2006/0224099 A1 * | 10/2006 | Hutchinson | A61M 1/3681 604/6.09 |
| 2006/0237351 A1 * | 10/2006 | Felding | A61M 1/1656 210/101 |
| 2006/0254982 A1 * | 11/2006 | Kopperschmidt | A61M 1/342 210/646 |
| 2006/0289360 A1 * | 12/2006 | Delnevo | A61M 1/3653 210/746 |
| 2007/0112297 A1 * | 5/2007 | Plahey | A61M 1/28 604/28 |
| 2007/0286756 A1 * | 12/2007 | Jones | F04B 43/1253 417/477.9 |
| 2008/0058712 A1 * | 3/2008 | Plahey | A61M 1/28 604/29 |
| 2008/0058727 A1 * | 3/2008 | Domash | A61M 39/10 604/174 |
| 2008/0097283 A1 * | 4/2008 | Plahey | A61M 1/28 604/29 |
| 2008/0105600 A1 * | 5/2008 | Connell | A61M 1/16 210/87 |
| 2008/0105601 A1 * | 5/2008 | Ikeda | A61M 1/16 210/96.2 |
| 2008/0208159 A1 * | 8/2008 | Stanus | A61J 1/10 604/408 |
| 2009/0105657 A1 | 4/2009 | Domash et al. | |
| 2010/0100034 A1 | 4/2010 | Wich-Heiter | |
| 2010/0133153 A1 | 6/2010 | Beden et al. | |

FOREIGN PATENT DOCUMENTS

| | | |
|---|---|---|
| DE | 10053441 A1 | 5/2002 |
| DE | 10224750 A1 | 12/2003 |
| DE | 10200411461 A1 | 9/2005 |
| DE | 102007018362 A1 | 10/2008 |
| DE | 102007042964 A1 | 3/2009 |
| DE | 102009008346.4 A1 | 8/2010 |
| DE | 102009012632.5 A1 | 9/2010 |
| DE | 102009012633.3 A1 | 9/2010 |
| DE | 102009024469.8 A1 | 1/2011 |
| EP | 0980686 A1 | 5/2002 |
| FR | 2594340 A1 | 8/1987 |
| JP | S62-5355 | 1/1987 |
| JP | 2002177383 | 6/2002 |
| JP | 2003518964 | 6/2003 |
| JP | 2005508719 | 4/2005 |
| JP | 2005528168 | 9/2005 |
| JP | 2008272440 | 11/2008 |
| WO | WO 03/101510 A1 | 12/2003 |
| WO | WO 2005/087290 A1 | 9/2005 |
| WO | WO 2008/011220 A2 | 1/2008 |
| WO | WO 2010/102784 | 9/2010 |
| WO | WO 2010/102790 A2 | 9/2010 |
| WO | WO 2011/015309 A2 | 2/2011 |

OTHER PUBLICATIONS

Japanese Search Report in Japanese Application No. 2012-506399, dated Jan. 7, 2014, 44 pages (with English translation).
Japanese Search Report in Japanese Application No. 2015-043678, dated Jan. 7, 2014, 11 pages (with English translation).

* cited by examiner

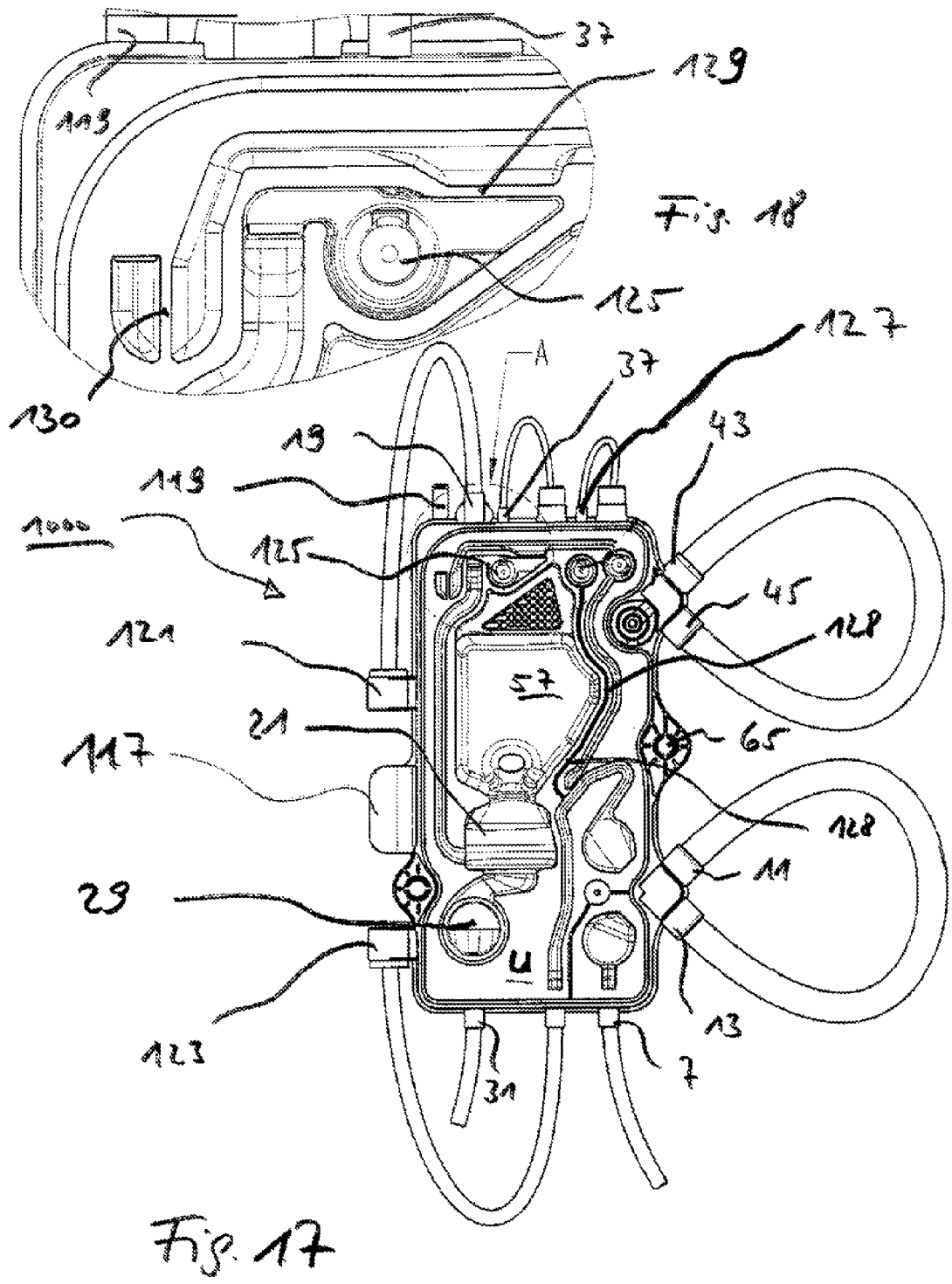

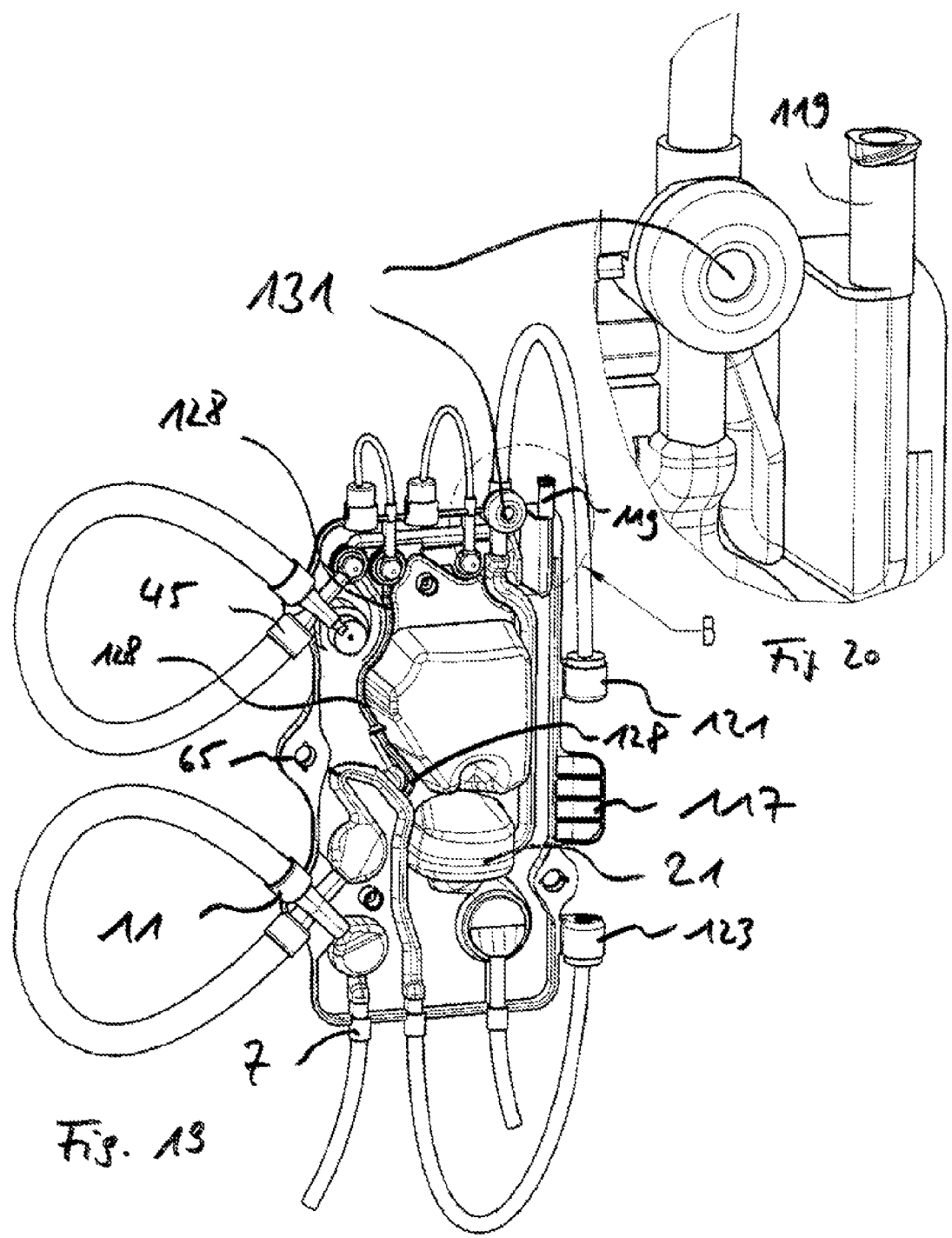

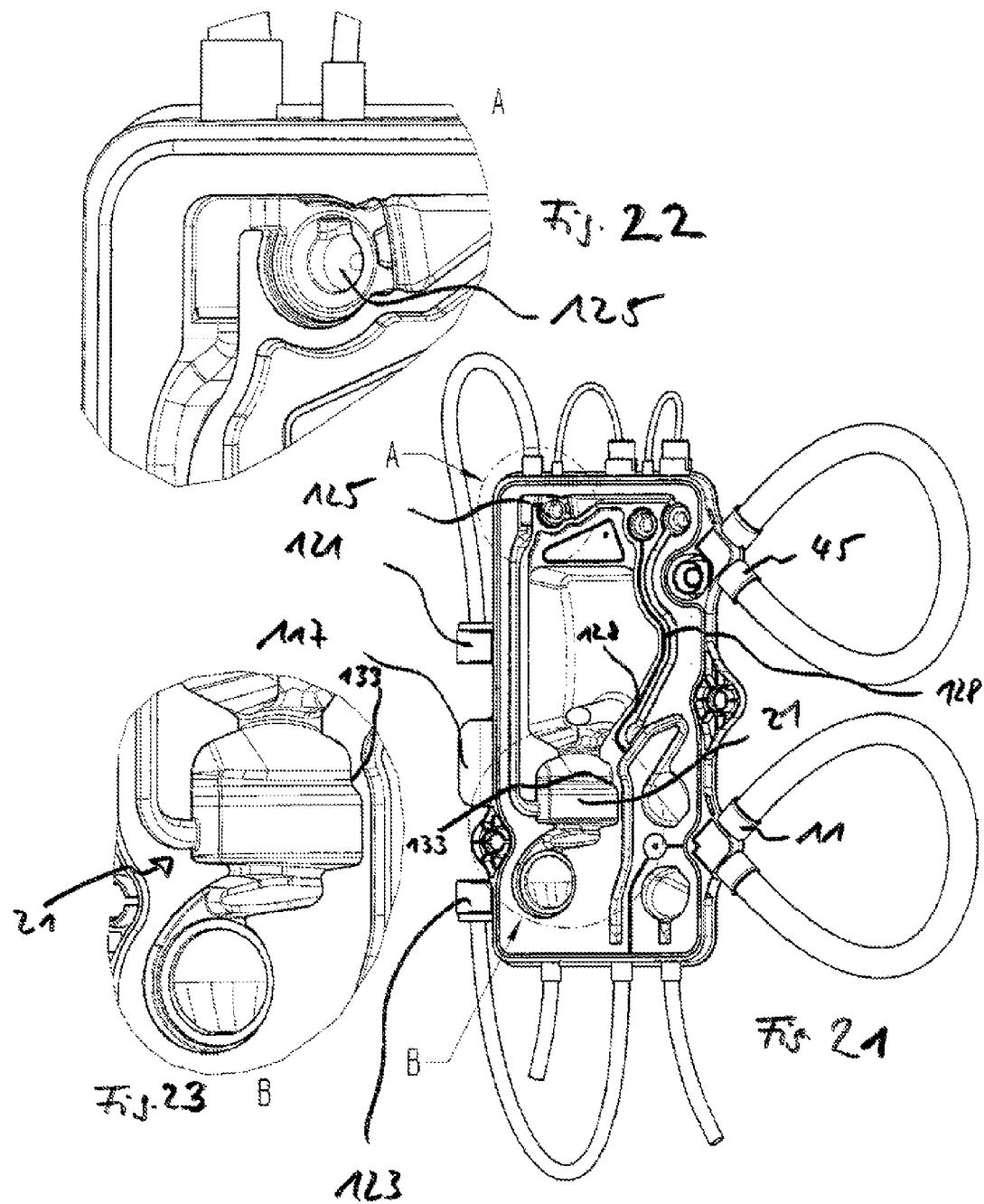

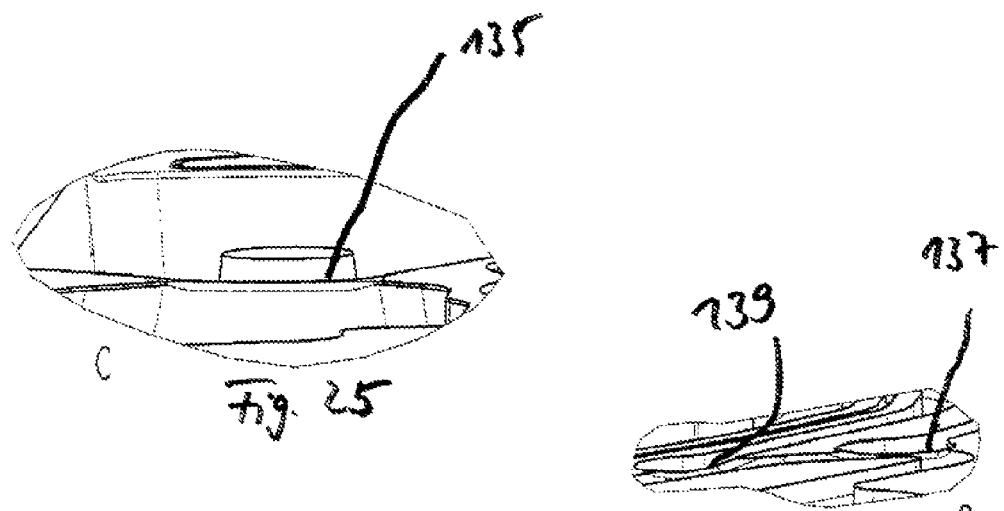
Fig. 25
Fig. 26
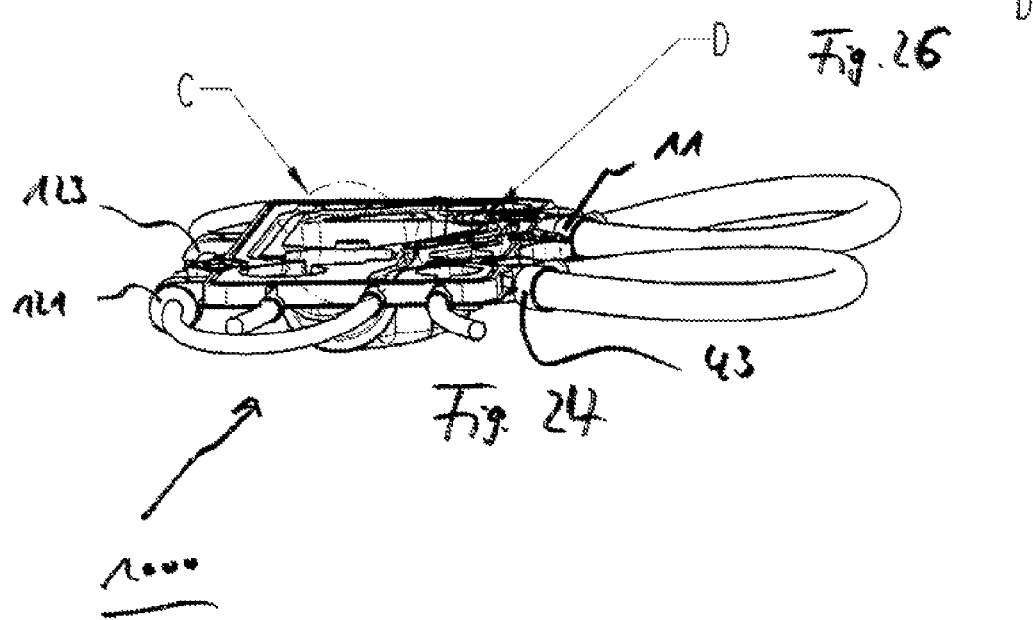
Fig. 24

EXTERNAL FUNCTIONAL MEANS, BLOOD TREATMENT APPARATUS FOR RECEIVING AN EXTERNAL FUNCTIONAL MEANS IN ACCORDANCE WITH THE INVENTION, AND METHOD

RELATED APPLICATIONS

This application claims the benefit of U.S. Provisional Patent Application No. 61/185,643, filed on Jun. 10, 2009, which is expressly incorporated herein in its entirety by reference thereto. Further, this application claims priority to German Patent Application No. 10 2009 018 664.6, filed on Apr. 23, 2009, and German Patent Application No. 10 2009 024 468.9, filed on Jun. 10, 2009, each of which is expressly incorporated herein in its entirety by reference thereto.

FIELD OF THE INVENTION

The present invention relates to an external functional means. It further relates to a blood treatment apparatus, as well as methods.

BACKGROUND

Cleaning of the equipment utilized in blood treatments may be technically complex. In order to guarantee sufficient hygiene at acceptable work expenditure as well as for other reasons, external functional means such as blood cassettes are employed.

Such a blood cassette may be adapted to fulfill as many functions as possible for the preparation and performance of blood treatment methods.

It is an object of the present invention to provide another external functional means, in particular a blood treatment cassette. Moreover it is intended to propose a blood treatment apparatus comprising a like external functional means or being adapted for driving and operating it, and corresponding methods for its use.

SUMMARY

The object of the invention is achieved through an external functional means having the features described herein.

The external functional means comprises at least one housing body, at least one chamber integrated into the housing body for receiving medical fluids, at least one passage integrated into the housing body for receiving and/or conducting a medical fluid, and at least one valve means completely or partly integrated into the housing body for controlling or regulating a fluid flowing through the external functional means.

The expression "housing body" as presently used designates a three-dimensional body and formed of a material that is suitable for use in a medical treatment method such as, for example, a blood treatment method, for example a plastic material. The housing body may, for example, be manufactured with the aid of a casting or injection molding method. The expression "chamber" as presently used designates a volume suited for receiving at least one medical fluid. The volume may be a closed space or may be defined by such a closed space. It may, however, also be an open space or be partly surrounded by such an open space, and only become a closed space—or a space closed with the exception of supply and discharge conduits for the fluid—as a result of the presence of some other body, namely, a body other than the housing body.

Chambers may be adapted and intended for receiving valves and/or sensors, or the like.

The expression "passage" or "conduit" as presently used designates a means that is suited for receiving and/or conducting medical fluids such as, for example, blood, heparin or other medicaments, saline solution, substituate, and the like.

Passages or conduits may be configured as closed and/or semi-open structures in portions thereof. They may, for example, be adapted for being closed on at least one open side by means of cover means and thus be configured to be sealable against, for instance, components of a blood treatment apparatus and/or against the atmosphere.

The expression "valve means" as presently used designates a structure, e.g., a valve, suited for controlling or regulating which may control the admission or passageway of fluids through passages or conduits and/or chambers of the external functional means. Valve means may be driven by means of control or regulation means provided for this purpose. Driving may, for example, take place in an automated manner. Suitable control or regulation means may, for example, be provided in or on the blood treatment apparatus.

Advantageous embodiments or developments of the external functional means of the invention are disclosed herein.

According to certain embodiments of the invention, a functional means is a structure via which functions such as conducting fluid by means of lines, valves, clot trapping and/or the like can be realized.

According to some embodiments of the invention, an external functional means is not a permanent part of a treatment apparatus. Rather, an external functional means according to these embodiments is connected with the treatment apparatus for the purpose of a treatment from external.

In a preferred embodiment, the external functional means is provided on at least one of its surfaces with a cover means which is part of at least one integrated valve means.

In another preferred embodiment, the cover means is connected by frictional and/or by form closure and/or by material connection with the housing body in at least a portion thereof. The cover means may, for example, be connected to the housing body by means of a peripheral weld or some other type of peripheral connection. Other non-peripheral or dot-shaped or local welds or connections (e.g., bonded or pressed connections) of the cover means with the housing body may also be provided.

In certain embodiments according to the invention, the cover means is—in certain ranges or areas thereof, respectively—connected with the external functional means, in particular with the housing body, along two sides or bilaterally of, respectively, structures (at least one structure) of the external functional means. According to the invention, the term "along or at both sides" or "bilaterally" may be understood as being present at least on two sides of the respective structure. A bilateral connection may be understood as an at least twofold connection in the section, in particular in the adjacent section, or in the environment or surrounding area, respectively, of the structure, in particular in close proximity.

Among these structures are, inter alia, fluid channels, lines, or other elements of the external functional means. Preferably, those elements are open in a cross-section perpendicular to the main extension plane of the cover means and/or are covered by means of the cover means against an outside or the atmosphere.

The bilateral connection can be a weldseam. It can be fluid-tight in each case, e.g., such that fluid, in particular, liquid is not exchanged through the joining area (the area in which, e.g., the bonding or weldseam has been made). The bilateral connection may be provided along single fluid channels, lines or other elements, e.g., in selected areas of the external functional means; it can be provided for a plurality thereof or for all fluid channels, lines or other elements.

A bilateral connection may be provided both at the left side and at the right side of the respective structure. It can be provided both at the top and at the bottom with respect to the structure, or the like.

A bilateral connection may be one, two or more weldings seams along the border or edge, respectively, or periphery or the extensions of at least one structure or a section thereof.

A bilateral connection may be completely or in partly extended lengthwise.

In certain embodiments according to the invention, by means of the bilateral connection, the complexity required for pressing the external functional means can advantageously be reduced. In some embodiments according to the invention, in particular the requirements for the precision with which the pressing of the external functional means on, e.g., a blood treatment apparatus is effected can advantageously be reduced. In certain embodiments according to the invention, due to the bilateral connection, a lower pressing pressure can advantageously be sufficient. In some embodiments according to the invention, there can advantageously be achieved a more reliable functioning of valves acting on channels covered by means of the bilateral connection.

A cover means may in particular be a film.

The film may preferably be a plastic film. For this purpose and in a preferred manner any laser-weldable film appearing appropriate to the skilled person may be considered.

In another preferred embodiment, the external functional means may comprise connections for being connected to an extracorporeal circuit in fluid communication.

The external functional means may in particular be configured as a cassette for a blood treatment.

In a further preferred manner, the external functional means may be adapted to be connected in fluid communication to at least one—preferably two—peristaltic pump(s) by means of two connectors. Roller pumps may be suitable peristaltic pumps.

The external functional means may comprise at least one—preferably two—pump tube segment(s), or may be configured or provided for receiving such a pump tube segment.

In another preferred embodiment, the external functional means comprises at least one valve means which comprises at least one bar and a portion of the cover means. The bar is formed on the housing body. Bar and cover means are disposed for being operated by means of an actor of a blood treatment apparatus acting on a bar, in order to alter a passage of fluid in a valve-like manner.

Such a "bar" may designate a component that is integrated into the external functional means or projects from a surface thereof in any desired direction. It may be formed of the same material as the external functional means. A web may, for example, be formed during the manufacture of the external functional means by means of casting or injection molding methods.

In another preferred embodiment, the fluid flowing through the external functional means during use thereof is a substitute, heparin, or some other pharmacologically active agent, saline solution (in particular 0.9% NaCl solution), blood, air, as well as combinations thereof.

The external functional means may in particular be adapted for being coupled to a blood treatment apparatus. In a further preferred manner, it may be configured and intended for being coupled to the blood treatment apparatus by means of a reception means of the blood treatment apparatus. The external functional means may in particular be adapted to be coupled to the treatment apparatus at the surface facing the cover means.

In another preferred embodiment, the external functional means may be adapted to be coupled to the blood treatment apparatus at an angle of rearward inclination of preferably between 5 degrees and 11 degrees, in particular at an inclination angle of substantially or precisely 8 degrees, relative to a vertical. The external functional means is preferably inclined to the rear in an upper region thereof (in the condition of use).

In another preferred embodiment, the external functional means comprises at least one substituate addition site including a touch-protection element and/or a drip-protection element. Other portions, in particular every other portion, of the external functional means may also comprise a touch-protection element and/or a drip-protection element.

A closure function of the ports (one, some, or all ports) of the external functional means may also be realized by means of septa or check valves.

The drip-protection element may be realized, for example, by an integrated closure sleeve.

The drip-protection element may preferably serve to prevent substituate or blood or a mixture of substituate and blood from dripping or trickling out from the reception means of the blood treatment apparatus during disassembly of the external functional means. In this way, hygienic handling of the used and impure external functional means may further be ensured outside of the treatment apparatus.

The external functional means in accordance with the present invention may be suited for use in a blood treatment method employing a double-needle access or a single-needle access.

The patient's blood is preferably already being conducted through the dialyzer during the phase of withdrawal from the patient, dialyzed in the process, stored in the single-needle chamber (preferably immediately) after its passage through the dialyzer, and from there returned to the patient in the returning phase. In this case, the blood is dialyzed in the "fresh" condition in which it leaves the patient. Thus, the method performed for a blood treatment by means of the cassette in accordance with the invention may advantageously differ from those conventional methods in which blood is taken from the patient, stored in a separate single-needle chamber, subsequently dialyzed, and returned to the patient via a venous air separator.

The external functional means may preferably comprise at least one single-needle chamber in which a blood surge redirection element is disposed.

A like "blood surge redirection element" or blood surge element may be suited and intended for achieving a flow deceleration, for generating a turbulence and/or redirecting the blood flowing into the single-needle chamber, or for cancelling the impulse of the blood surge. A like blood surge redirection element may in particular be configured in a rheologically optimized manner. It may, for example, be configured in the shape of an ellipsoidal or round column which is connected to a wall of the single-needle chamber on at least one portion of its circumference.

Without a blood surge redirection element, a blood surge flowing in through the phantom valve might in a given case cause gushing. This might lead to hunting movements or sloshing movements, respectively, of the liquid level and/or to formation of foam. By means of the blood surge element the total blood surge is divided into two smaller blood surges, whereby the impulse of the total blood surge may be cancelled, and gushing, sloshing movements and/or formation of foam may advantageously be avoided.

As a blood surge redirection element, it is preferably possible to use a blood surge redirection element as disclosed by the applicant of the present invention in German Patent Application No. 10 2009 024 466.2 having the title "Aufnahmeeinrichtung zum Aufnehmen von medizinischen Fluiden sowie externe Funktionseinrichtung and medizinische Behandlungsvorrichtung" [Reception means for receiving medical fluids, as well as external functional means and medical treatment apparatus] as filed with the German Patent and Trademark Office on Jun. 10, 2009, and U.S. Provisional Patent Application No. 61/185,607, also filed on Jun. 10, 2009. The relevant disclosures thereof are herewith fully incorporated by way of reference thereto.

The external functional means of the present invention may preferably comprise at least one venous blood chamber.

The single-needle chamber may preferably be arranged above the venous blood chamber, relative to the orientation of the external functional means during its use.

The venous blood chamber may be subdivided into at least one upper space and at least one lower space by means of a cross-sectional restriction of the housing body.

The upper space and the lower space may be in fluid communication or connection with each other.

The upper space may be configured so as to allow or generate a tangential inflow of fluids flowing through the external functional means. The upper space may comprise a region for generating a stable rotational flow of the fluids flowing through the external functional means.

The lower space may comprise a region that is substantially or entirely free from rotational flow of the fluids flowing through the external functional means.

In a preferred manner, walls or wall portions of the upper space and/or of the lower space of the venous blood chamber may be adapted to an inclination of the external functional means against a vertical of the blood treatment apparatus. This may advantageously allow the blood to flow or stream or pass through the venous blood chamber in a rheologically optimized manner. Furthermore, air possibly contained in the blood can ascend and thus being separated in an appropriate manner.

The venous blood chamber may be configured to have an air separator effect, as was disclosed by the applicant of the present invention in German Patent Application No. 10 2009 024 465.4 having the title "Luftabscheider, externe Funktionseinrichtung, Blutkreislauf sowie Behandlungsvorrichtung" [Air separator, external functional means, blood circuit, and treatment apparatus] as filed with the German Patent and Trademark Office on Jun. 10, 2009, and U.S. Provisional Patent Application No. 61/185,608, also filed on Jun. 10, 2009. The relevant disclosures thereof are herewith fully incorporated by way of reference thereto.

In another preferred embodiment of the external functional means, the housing body is configured as a hard part.

The hard part may be a housing body which is substantially formed integrally and out of one material. This housing body may be an injection-molded part. It may have a minimum stiffness of more than 400 N/mm$^2$, in a preferred manner 1200-1800 N/mm$^2$ (bending modulus of elasticity).

In another preferred embodiment of the external functional means as a blood treatment cassette, it is in a further preferred embodiment possible to measure the pressure in the extracorporeal blood circuit upstream of the dialyzer across the cover means or film.

The external functional means may preferably be a single-use article which is disposed after having been used once.

The object of the invention is also achieved through a blood treatment apparatus as described herein.

In a preferred embodiment, the blood treatment apparatus is configured for receiving at least one external functional means in accordance with the present invention.

In another preferred embodiment, the blood treatment apparatus comprises at least one control means and/or actors and/or sensors for driving and/or operating the external functional means.

The control means may be configured as a CPU or a part thereof.

The control means and/or the actors may be suited and intended, e.g., for operating or driving, e.g., controlling or regulating, a valve means. They may be arranged at a position of the blood treatment apparatus opposite to a valve means of the external functional means in the coupled state thereof.

In another preferred embodiment, the blood treatment apparatus comprises at least one reception means for receiving at least one external functional means in accordance with the present invention. The reception means may comprise a coupling surface for coupling the external functional means in accordance with the present invention. Such a coupling surface may, for example, be inclined at an angle against a vertical relative to the orientation of the blood treatment apparatus during its use, in particular to the rear. Such an angle may be between 5 and 11 degrees, in particular substantially or precisely 8 degrees.

The blood treatment apparatus may be suited for performing a method or a method step, as will be described in the following and by making reference to the figures.

In another embodiment, the blood treatment apparatus comprises a control means—e.g., in the form of a CPU—for operating or regulating an external functional means in accordance with the present invention and/or for performing a method or a method step, as will be described in the following and by making reference to the figures.

Furthermore, the blood treatment apparatus may comprise at least one actor for operating an external functional means in accordance with the present invention or a portion thereof for performing a method or a method step in accordance with the present invention.

The blood treatment apparatus may in particular also comprise sensors in form of information providers, wherein the information serves as signals for the control unit for operation of an external functional means in accordance with the present invention for performing a method or a method step in accordance with the present invention.

The blood treatment apparatus may, for example, be a dialyzing means.

The blood treatment apparatus may comprise a control means for measuring a parameter present in the extracorporeal circuit or in the blood circuit of the external functional means of the invention that is configured as a blood treatment cassette such as, for example a pressure, a differential pressure, and the like.

The differential pressure may be measured between the cassette-integrated arterial chamber and the cassette-integrated venous chamber. The differential pressure may be used as a measure for the blood-side pressure difference of the dialyzer. The control means of the blood treatment apparatus may be configured for calculating the difference, in a given case for comparing the pressure difference to reference values (which may be deposited, for example, in the control means or in a memory), and optionally for outputting control signals.

Here it is, for example, advantageously possible to recognize an onset of clogging of the dialyzer early on or in due time. Countermeasures may be taken.

These may include or consist of the addition of anti-coagulants such as, e.g., heparin, e.g., via the cassette-integrated addition sites.

Furthermore, it is, e.g., possible to increase the pre-dilution. It is possible to switch over from post-dilution to pre-dilution.

The cassette-integrated measurement sites may furthermore advantageously enable a transmembrane pressure measurement across the dialyzer membrane.

To this end, four measurement sites may be provided where measurements are performed with the aid of corresponding means, and the measurement results of which are evaluated with the aid of suitable means: one at the filter inlet and one at the filter outlet, i.e., at the blood side and at the dialysate side, respectively.

In some embodiments according to the invention, the external functional means is—in certain sections thereof—(at least also) in one direction perpendicular to the coupling plane (or to a main section thereof) thicker than other sections. The thicker sections—of which one or more can be provided—serve for receiving measurement devices such as, e.g., optical measurement devices, ultrasonic devices, temperature measurement devices, and the like.

Sections of the external functional means which are not thicker but which primarily extend in the main extension plane of the external functional means, preferably in parallel to a main coupling plane of the external functional means and/or in parallel to an actuator-sensor-plate of the treatment apparatus, can have the same effect. Those sections (one or more) extending the external functional means can likewise be thicker; however, according to the invention, this is not necessary.

The measurement devices can be connectable or connected with the treatment apparatus from a side of the door of the treatment apparatus by means of which door, in certain embodiments according to the invention, the external functional means is pressed with the treatment apparatus and/or covered for the purpose of its use.

The measurement devices can be connectable or connected with the treatment apparatus from a side of an actuator-sensor-plate of the treatment apparatus by means of which plate, in some embodiments according to the invention, a functional or signal connection is established between the external functional means and the treatment apparatus.

The measurement device arranged in such thicker or longer sections can, for example, serve for measuring conditions or states, respectively, within supplying or discharging fluid channels of the external functional means (in particular fluid channels discharging a fluid out of the external functional means or fluid channels supplying a fluid to or into the external functional means). They can be arranged in close proximity to such fluid channels.

All or some of the thicker or longer sections are preferably provided in a border or rim area of the external functional means. This can advantageously enable a simple connection between the measurement device respectively present in one of the afore-mentioned sections and the treatment device. Furthermore, such an arrangement in a border or rim area can allow for an easy access.

The external functional means can comprise measuring points, for coupling detectors such as, e.g., optical detectors for detecting line or valve leakage, in the afore-mentioned thicker or longer sections or at other positions. Such a leakage could happen, e.g., in the proximity of the phantom valves, the non-return valves, in the supplying or discharging lines (e.g., leading towards the valves or away from the valves), or the like. The measuring points and/or the, in particular optical, detectors can be arranged at corresponding positions.

In some embodiments according to the invention, the external functional means can comprise one or more addition sites each comprising at least one septum. The septum can be designed for being easily penetrated during addition; however, it advantageously provides sealing and thus safety and tightness.

Preferably, the addition sites are integrated into the external functional means or are integral therewith.

The addition sites can be arranged in an end area or a border area of the external functional means. In some embodiments according to the invention, such an arrangement can advantageously allow for an easy access to the addition sites. In certain embodiments according to the invention, this particularly applies for a case in which the external functional means is in contact (e.g., pressed) with a treatment apparatus both at its front side and at its back side for the purpose of coupling therewith and thus both reaching the front and the back side for an addition by means of the septum is cumbersome or difficult. Therefore, in some embodiments, ergonomic advantages can be obtained.

In further preferred embodiments, supplying lines can be arranged at or in the external functional means such that the supplying line (completely or partly) or a connection site (such as a connection port of the supplying line) to or with the supplying line are present in an upper area of the external functional means—preferably with respect to an intended or conventional, respectively, position or arrangement of the external functional means during its intended or conventional, respectively, use (e.g., in a state in which it is pressed with the treatment apparatus).

The upper area can be a border or rim area. The upper area can be an area above a coupling surface or a coupling area.

The supplying line may be a line for an anticoagulant. It may be a heparin line. A respective syringe pump for the anticoagulant, e.g., heparin, may be arranged above the external functional means or the coupling plane thereof during use of the external functional means.

Advantages which can be achieved in some embodiments according to the invention also comprise ergonomic advantages, furthermore advantages resulting from a shorter supplying line, improved accessibility of the connection site, and so on.

Supplying lines can in some embodiments be understood as lines through which fluids can be supplied to the extra-corporeally flowing blood during use of the external functional means in a blood treatment or which are provided therefore.

The blood treatment apparatus may comprise a control means for operating the cassette valves. The control means may preferably switch over between the cassette-integrated pre- and post-dilution in a freely programmable manner. It may preferably alter the substitute stream (volume flow).

Information providers may in particular be the cassette-integrated pressure measurement sites arranged up- and downstream of the dialyzer.

The object of the invention is furthermore achieved through the methods of the invention disclosed herein. The methods shall be explained in the following.

By way of example, the blood treatment method shall in the following be assumed to be a dialyzing method such as a hemodiafiltration. The blood treatment apparatus is, for example, a dialyzing means.

The dialyzing means comprises an extracorporeal circuit having an arterial and a venous portion. The dialyzing means further comprises an arterial and a venous patient tube clamp.

During dialysis, a patient is connected to the extracorporeal circuit via a patient's access such as, for example, a fistula, a shunt or graft, or a catheter exemplarily having the form of a double-needle access or of a single-needle access.

The extracorporeal circuit may comprise a blood pump for conveying blood as well as a substitute pump for conveying substitute, and corresponding pump tube segments.

The blood pump and the substitute pump may be configured as peristaltic pumps, for example roller pumps.

A "conveying direction" or "direction of flow" of the blood during a dialysis treatment designates a direction in which the blood to be purified is usually conveyed. In particular it may designate a direction running from the patient via an arterial needle, an arterial portion, a dialyzing means (in the figures from bottom to top), a venous portion, and may return to the patient via a venous needle.

A conveyance of fluid (in particular blood and/or substituate) taking place against this conveying direction is referred to as a conveyance, or flow, in the opposite direction.

The blood treatment apparatus comprises a dialyzing means having a dialyzing liquid inlet and a dialyzing liquid outlet, wherein the dialyzing liquid may be conveyed through the dialyzing means in a direction opposite to the blood (in the figures from top to bottom).

A substitute may be introduced or administered into the extracorporeal circuit through a substitute addition site and through a pre-dilution addition valve and/or a post-dilution addition valve.

The expressions "clockwise" or "counter-clockwise" refer to the figures. A blood pump and a substitute pump usually convey in a counter-clockwise direction, as may correspond to the usual conveying direction during a dialysis treatment.

During priming or filling, the pre-dilution addition valve, the post-dilution addition valve, and a single-needle blood valve may initially be in the open state each.

In a preferred manner, the arterial patient tube clamp and the venous patient tube clamp are also open.

The arterial patient connection and the venous patient connection are preferably connected to each other.

A plug valve, which is a machine-side valve (also known as a "rinse port") through which a fluid connection between the extracorporeal circuit and the atmosphere or a collecting container may be established and through which fluids flowing through the external functional means may be discharged from the extracorporeal circuit, is preferably also closed.

Substitute is added via the substitute addition site.

The substitute pump is started; it is preferably operated in a counter-clockwise direction (relative to the plane of drawing of the annexed figures). The blood pump is started, preferably in the clockwise direction.

Substituate is preferably conveyed as far as, or to a position before the post-dilution addition valve. The post-dilution addition valve is preferably closed upon arrival.

Substituate is conveyed through the pre-dilution addition valve, preferably in a direction towards the dialyzing means and/or in a direction towards the blood pump.

The substituate flowing towards the dialyzing means may pass through the dialyzing means and the venous portion of the extracorporeal circuit and enter a venous blood chamber of the external functional means.

The substituate flowing toward the blood pump may pass through the pump tube segment inserted in the blood pump in a clockwise direction. In a preferred manner, the substituate further flows through the connection between arterial and venous patient connections, passes through a clot trap of the external functional means, and arrives in the venous blood chamber.

At or in the clot trap, in accordance with the invention it is possible to measure the pressure in the extracorporeal circuit by means of an appropriate pressure measuring means. This may preferably be performed across a cover means of the external functional means which is configured, e.g., as a blood treatment cassette. If it is configured as a film, the measurement may be performed across the film or through the intermediary of the film. In this way, it is thus preferably possible to measure the pressure in the extracorporeal circuit, particularly following passage through the dialyzer.

Here, it is possible for the substituate flowing towards the dialyzing means to be mixed in the venous blood chamber with the substituate flowing towards the blood pump.

Once the venous blood chamber is filled, the pre-dilution addition valve and the single-needle blood valve may preferably be closed or close automatically.

The substitute pump preferably stops or is stopped. The pre-dilution addition valve, the post-dilution addition valve and the single-needle blood valve are preferably closed.

Substitute is conveyed through the extracorporeal circuit by operating the blood pump. Preferably no substitute or only a small quantity of substitute is present in the single-needle chamber.

In accordance with the invention, the on-line filling procedure may also be carried out as follows:

1. Connecting the automatic substitute connector.
2. Arterial and venous patient tubes are connected to a rinse port of the blood treatment apparatus, e.g., by means of a suitable connector providing an appropriate access from one end of the one patient tube to the other patient tube. The end of the other patient tube serves as a drain conduit to the rinse port. The connector may alternatively be located in the arterial or venous patient conduit.
3. The venous patient tube clamp is closed, the post-dilution valve is opened, the pre-dilution valve is closed.
4. Filling the venous chamber with the aid of the substitute pump through the post-dilution valve, with separation of air taking place through the single-needle valve.
5. The blood pump operates in a forward direction and aspires or sucks in substitute from the venous chamber.
6. When the level in the venous chamber drops, replenishing via the post-dilution valve is performed until the level detector recognizes that the predetermined filling level is exceeded. During this process, which is repeated according to need, continuous operation of the blood pump is maintained.

7. De-aerating the clot trap "from below": All three cassette valves are closed. The arterial clamp is opened and the venous clamp is closed. The rinse port is closed.
8. The blood pump operates in the reverse direction for a short time to convey a small volume. Hereby a venous negative pressure and an arterial overpressure are generated in the extracorporeal blood circuit.
9. Opening the venous clamp until a pressure equilibrium is established.
10. Continuing filling of the extracorporeal blood circuit.
11. Rinsing the filled extracorporeal blood circuit: The occurrence of air bubbles is detected by means of the venous air bubble detector. Once no air bubbles or virtually no air bubbles are detected in the course of a predetermined time interval, the extracorporeal blood circuit is assumed to be filled.
12. During rinsing, substituate is conveyed through the pre-dilution valve and discarded through the rinse port ("plug valve").
13. Both the arterial and the venous clamp are opened here. The blood pump operates in the reverse direction and conveys a part of the substituate into the rinse port.

As an alternative for on-line filling (where the substituate is supplied on-line in the dialysis machine) it is also possible to perform filling with an external bag containing saline solution as a source for the filling liquid. To this end, the arterial patient conduit is connected to the bag containing saline solution. The venous patient conduit is connected to a so-called waste bag as a sink for the used saline solution. The blood pump operates in the forward direction. By opening the pre-dilution valve and the post-dilution valve, it is also possible to fill the conduit situated between these two valves.

In both methods, the patient is connected to the extracorporeal blood circuit not before a predetermined rinsing quantity has been reached.

In rinsing, preferably the pre-dilution addition valve, the post-dilution addition valve as well as the single-needle blood valve are initially closed.

The arterial patient tube clamp and the venous patient tube clamp are preferably open at the beginning.

The arterial patient connection and the venous patient connection are still connected to each other.

Substituate is conveyed through the extracorporeal circuit by operating the blood pump, wherein, for example, no substituate is present in the single-needle chamber.

The pre-dilution addition valve is now preferably opened, likewise the plug valve (a machine-side valve or a "rinse port").

By operating the substituate pump (preferably in the counter-clockwise direction of the plane of drawing) and the blood pump (preferably in the clockwise direction), substituate is preferably conveyed continuously through the extracorporeal circuit. The blood pump may rotate more slowly than the substituate pump.

The substituate may exit from the extracorporeal circuit via a drain conduit in order to be discarded.

In order to perform a dialysis, a patient is connected to the extracorporeal circuit. The connection may, for example, be achieved with the aid of a double-needle access or with the aid of a single-needle access.

In a first variant of a patient connection, the pre-dilution addition valve, the post-dilution addition valve, and the single-needle blood valve may preferably be closed.

A patient may be connected to the extracorporeal circuit by means of a double-needle access via an arterial needle and a venous needle.

In a preferred manner, the arterial patient tube clamp and the venous patient tube clamp may initially be closed.

Then, the arterial patient tube clamp may be opened.

The blood pump may be operated (preferably in a counter-clockwise direction) and preferably convey blood through the arterial needle into the extracorporeal circuit.

Substituate may be discharged at the dialyzing liquid outlet from the extracorporeal circuit in order to be discarded.

When the blood to be purified arrives at a blood inlet at the dialyzing means, the arterial patient tube clamp may preferably be closed and the venous patient tube clamp may then be opened.

The blood pump may be stopped.

Now, blood may preferably flow through the venous needle into the extracorporeal circuit and through the clot trap into the venous blood chamber and through a venous filter conduit to a blood outlet out of the dialyzing means.

According to a second variant, a patient may alternatively be connected to the extracorporeal circuit via a patient connection.

At first the pre-dilution addition valve, the post-dilution addition valve, and the single-needle blood valve will preferably be closed.

The patient may, for example, again by means of a double-needle access, be connected to the extracorporeal circuit via an arterial needle and a venous needle.

The blood pump may now be operated (preferably in the counter-clockwise direction) and convey blood through the arterial needle into the extracorporeal circuit. The blood may preferably flow through the dialyzing means and the external functional means. The blood may preferably enter the patient via the venous needle.

The arterial and venous patient tube clamps may preferably stay open.

In a dialysis treatment without addition of substituate, the pre-dilution addition valve and the post-dilution addition valve may be closed. When performing a dialysis treatment by using a double-needle access, the single-needle blood valve may preferably be closed.

Furthermore, the arterial patient tube clamp and the venous patient tube clamp are preferably open, so that blood may flow continuously through the extracorporeal circuit. In a preferred manner, the blood pump may convey the blood through the arterial needle into the extracorporeal circuit and through the venous needle back to the patient.

The blood flows through the dialyzing means where it may advantageously be purified with the aid of the dialyzing liquid flowing through the dialyzing means in the opposite direction to the blood.

In a preferred manner both steps—i.e., arterial suction and venous suction—may take place in parallel—at least over a period of time.

The expression "on-line HDF pre-dilution" designates a dialyzing method, in particular a hemodiafiltration, in which substituate is added to the blood to be purified.

In this method ("on-line HDF pre-dilution") the pre-dilution addition valve may preferably be open, while the post-dilution addition valve and the single-needle blood valve may in turn be closed.

The arterial patient tube clamp and the venous patient tube clamp may preferably be opened.

The blood pump (preferably operating in the counter-clockwise direction) may convey blood through the arterial needle into the extracorporeal circuit and through the venous needle back to the patient or into the vascular system thereof, as was already described in the foregoing with regard to a dialysis treatment.

The substitute pump (preferably operating in the counter-clockwise direction) may convey substitute which may mix up with the blood at or starting from the pre-dilution addition valve in the arterial portion of the extracorporeal blood circuit.

In accordance with the above description, the dialyzing liquid may preferably be conducted through the dialyzing means in an opposite direction to the blood and may be used for purifying the blood equally flowing through the dialyzing means.

The expression "on-line HDF post-dilution" designates a dialyzing method, in particular a hemodiafiltration, in which substituate is added to the purified blood.

In a preferred manner, the post-dilution addition valve may here be open, with the pre-dilution addition valve and the single-needle blood valve, on the other hand, being closed.

The process sequence substantially corresponds to the sequence of the above-described "on-line HDF pre-dilution", with the exception that the substitute may be added to the purified blood at or starting from the post-dilution addition valve in the venous portion and mixed up with it.

A so-called "on-line HDF mixing dilution" designates a process in which it is possible to switch over between a process of "on-line HDF pre-dilution" as described in the foregoing, and a process of "on-line HDF post-dilution" as described in the foregoing.

Here, each partial process of pre-dilution or post-dilution may be maintained for a particular time interval. Each partial process may be repeated continuously.

The temporal proportions of pre- or post-dilution may be in fixed or variable ratios and may be varied as a function of a measured quantity.

As an alternative for a blood treatment by using a double-needle access to the patient as described in the foregoing, the blood treatment may be carried out by using a single-needle access ("Cassette Integrated Single Needle").

A single-needle access may comprise a Y-shaped branching into the arterial portion and the venous portion of the extracorporeal circuit.

The pre-dilution addition valve and the post-dilution addition valve may be closed. The single-needle blood valve, on the other hand, may preferably be opened. In this way, a fluid communication between the venous blood chamber and a single-needle chamber may be possible.

The arterial patient tube clamp and the venous patient tube clamp may be closed.

The patient is connected to the extracorporeal circuit, and the arterial patient tube clamp may preferably be opened.

The blood pump may convey blood through the extracorporeal circuit via the venous blood chamber, preferably into the single-needle chamber of the external functional means.

When the single-needle chamber is substantially or entirely filled, the blood pump may preferably be stopped and the arterial patient tube clamp may be closed. Then, the venous patient tube clamp may be opened.

Blood may flow back into the patient's vascular system, or to the patient, through the venous portion.

Then, the arterial patient tube clamp is preferably opened. The process may be repeated as often as necessary and/or desired, either continuously or at particular intervals.

A combination of single-needle treatment with hemodiafiltration is equally possible.

Following a blood treatment method, the blood present in the extracorporeal circuit may preferably be recirculated into the patient after the treatment.

In a first variant of blood recirculation, the pre-dilution addition valve may be open and the post-dilution addition valve and the single-needle blood valve may be closed.

The arterial patient tube clamp may preferably be closed while the venous patient tube clamp on the other hand is opened.

The arterial needle and the venous needle of a double-needle access may preferably remain at or with the patient.

The substitute pump (preferably operating in the counter-clockwise direction) may be operated to preferably convey substitute through the pre-dilution addition valve into the extracorporeal circuit.

The substitute may flow through the dialyzing means and the venous portion of the extracorporeal circuit and displace the blood in the process. Shortly before the substitute reaches the venous needle, the substitute pump may preferably be stopped.

After this, the venous patient tube clamp may be closed and the arterial patient tube clamp may be opened.

The substitute pump (preferably operating in the counter-clockwise direction) and the blood pump (preferably operating in the clockwise direction) may be operated.

Starting from or at the pre-dilution addition valve, the substitute may be conveyed into the arterial portion towards the patient. Shortly before the arterial needle is reached, both pumps may preferably be stopped.

A return through the arterial and venous needles may also take place simultaneously. The substitute pump then operates in a forward direction at a higher rate, and the blood pump in a reverse direction at a lower rate.

In a second embodiment of the blood recirculation process, the pre-dilution addition valve, the post-dilution addition valve and the single-needle blood valve may be closed.

The arterial patient tube clamp and the venous patient tube clamp may preferably be closed.

In a preferred manner, at least one sensor/detector may be provided in the arterial part of the extracorporeal blood circuit, and at least one sensor/detector may be provided in the venous part of the extracorporeal blood circuit.

The arterial needle may be disconnected from the patient and/or the arterial patient conduit may be disconnected from the arterial needle. The arterial patient tube clamp and the venous patient tube clamp are preferably opened.

The blood pump (preferably operating in the counter-clockwise direction) may be operated to convey blood through the arterial needle into the extracorporeal circuit.

When the sensor/detector in the arterial part of the extracorporeal blood circuit detects the presence of air, the blood pump may preferably continue conveying until blood arrives at the pre-dilution addition valve. Then, the blood pump may preferably be stopped.

The arterial patient connection may be closed.

The substitute pump may be operated (preferably operating in the counter-clockwise direction).

The pre-dilution addition valve may be opened, and the substitute pump may preferably convey substitute through the pre-dilution addition valve into the extracorporeal circuit.

The substitute may flow through the extracorporeal circuit and preferably displace the blood present therein. When the sensor/detector of the venous patient tube clamp recognizes the presence of substitute, the substitute pump may preferably continue to convey blood and substitute through the venous needle into the patient until all of the blood has been recirculated from the extracorporeal circuit into the patient.

Finally, the venous needle may be withdrawn, and the pumps may preferably be stopped.

For emptying, the pre-dilution addition valve and the post-dilution addition valve may be open, the single-needle blood valve may however be closed.

The arterial patient tube clamp and the venous patient tube clamp may be closed.

The arterial patient connection and the venous patient connection may preferably be connected to each other.

At the beginning of the process, the arterial patient tube clamp and the venous patient tube clamp may be opened.

Substituate may preferably be introduced into the extracorporeal circuit at or via the substituate addition site. For emptying, air may be conveyed.

The substituate pump may be operated (in the counterclockwise direction) and convey substituate through the extracorporeal circuit towards the pre-dilution addition valve and the post-dilution addition valve.

Spent substituate may preferably exit from the extracorporeal circuit at the dialyzing liquid outlet in order to be discarded. The air may be conveyed to thereby displace the substituate.

The substituate may on the one hand be conveyed through the pre-dilution addition valve and on the other hand through the post-dilution addition valve towards the dialyzing means.

The pre-dilution addition valve may be closed. The blood pump may be started.

By operating the blood pump (preferably operating in the counter-clockwise direction) and the substituate pump (preferably operating in the counter-clockwise direction), air may be conveyed towards the dialyzing means through the extracorporeal circuit—beginning upstream from the post-dilution addition valve—through the venous blood chamber, the clot trap, the venous portion, and the arterial portion. It may preferably exit from the extracorporeal circuit through the dialyzing liquid outlet. The used substituate may be discarded.

In the following, the present invention shall be described by way of preferred embodiments thereof while making reference to the drawings.

BRIEF DESCRIPTION OF THE DRAWINGS

FIG. 17 shows in a simplified schematic representation an external functional means according to the invention in a further embodiment, in a view onto its front side.

FIG. 18 shows in a simplified schematic representation a detail of the representation of FIG. 17.

FIG. 19 shows in a simplified schematic representation the external functional means according to the invention in the further embodiment of FIG. 17 shown in a perspective view onto its back side.

FIG. 20 shows in a simplified schematic representation a detail of the representation of FIG. 19.

FIG. 21 shows in a simplified schematic representation the external functional means according to the invention in a view onto its front side.

FIG. 22 shows in a simplified schematic representation a detail of the representation of FIG. 21.

FIG. 23 shows in a simplified schematic representation a further detail of the representation of FIG. 21.

FIG. 24 shows in a simplified schematic representation one embodiment according to the invention of the external functional means.

FIG. 25 shows in a simplified schematic representation a detail of the representation of FIG. 24.

FIG. 26 shows in a simplified schematic representation a further detail of the representation of FIG. 24.

DETAILED DESCRIPTION

Figure 1:
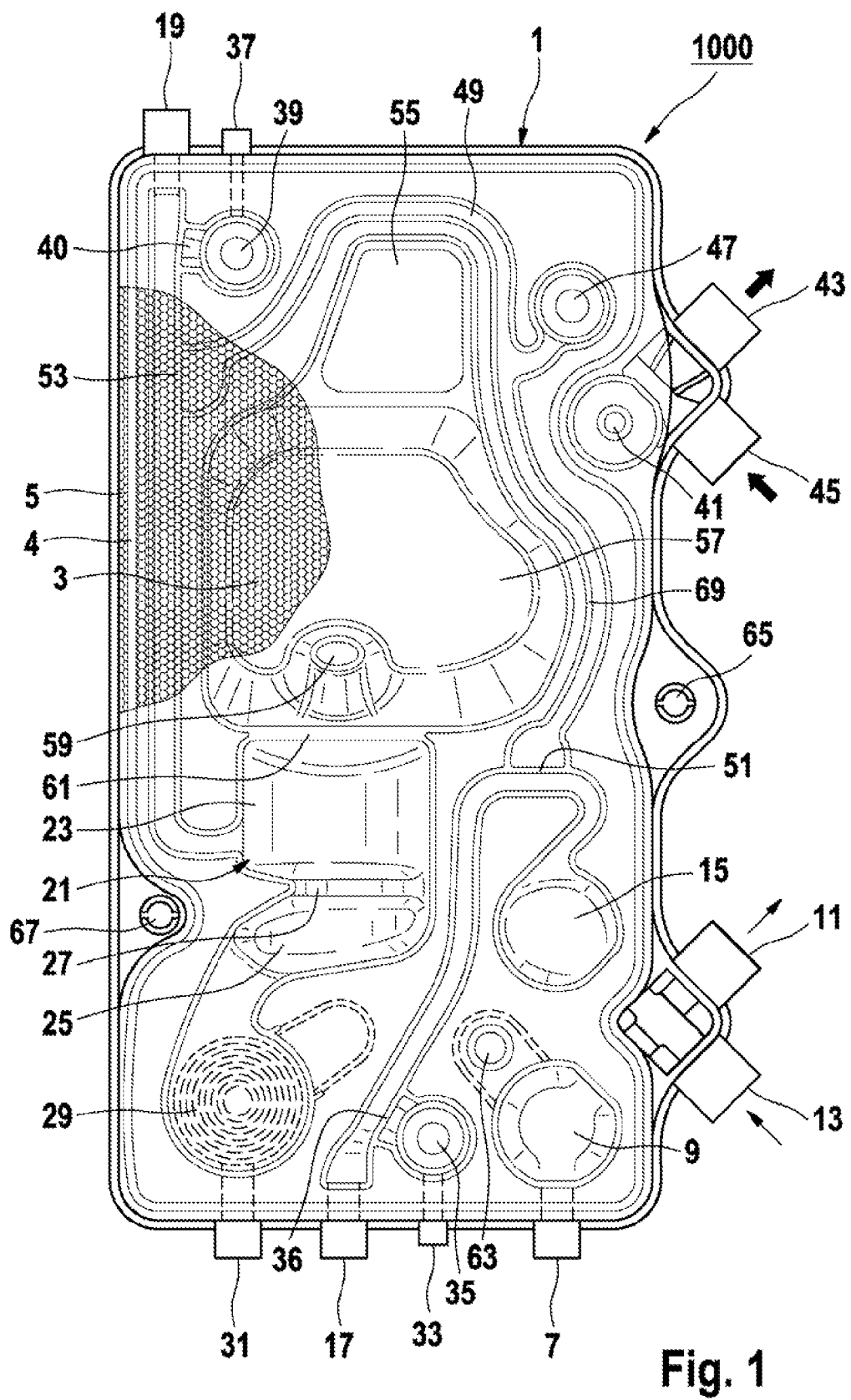
FIG. 1 shows a lateral view of an external functional means of the invention provided, in accordance with a preferred embodiment, having a cover means on its front side.

In the figures of the drawings, same reference numerals designate same or identical elements.

For an exemplary explanation of the present invention, a blood treatment apparatus is selected as a treatment apparatus, and a blood treatment method as a method.

The standard arrows in the figures indicate the direction of the blood stream. The block arrows indicate the respective direction of the substituate stream. The double block arrows indicate the respective direction of the dialyzing liquid stream.

FIG. 1 shows a lateral view of an external functional means which is provided with a cover means at the surface one looks upon in FIG. 1.

The external functional means is here exemplarily configured as a cassette 1000.

The cassette 1000 comprises a hard part 1. As is exemplarily shown in FIG. 1, the hard part 1 comprises chambers, passages and valves. As is furthermore exemplarily shown in FIG. 1, the chambers, passages and valves are integrated into the hard part 1 or are at least partly formed by the hard part 1.

The cassette 1000 of FIG. 1 is provided at its front side with a cover means, in the present case, for example, a film 3. The cover means may be welded in a flat manner, i.e., planarly, onto the hard part 1.

An embodiment involving a three-dimensional configuration of the weld and seal contour is also possible in accordance with the invention.

The cover means may close the chambers and/or passages of the hard part 1 of the cassette 1000, namely, against a side facing away from the hard part 1 of the cover means and/or against the atmosphere.

As may be seen in FIG. 1, the film 3 rests on the hard part 1 of the cassette 1000 at a peripheral sealing bar 4. The film 3 is welded with the hard part 1 of the cassette 1000 at a peripheral weld 5.

The peripheral sealing bar 4 may alternatively be realized in an exposed manner.

The film 3 may be connected to the hard part 1 of the cassette 1000 at additional local welds (not shown). These may also be peripheral, i.e., closed in the sense of a terminating limitation similar to a ring, and/or dot-shaped.

The film 3 may locally be connected, e.g., welded, with the hard part 1 of the cassette 1000 in form of a dot or a line, in particular at the marginal zones of the liquid-conducting passages.

The film 3 may be connected to the hard part 1 of the cassette 1000 by laser welding. Here, it is advantageous if the local application of heat is carried out by using light-absorbing components. The light-absorbing component(s) may be part of the material of the film and/or of the hard part, or a layer disposed between film and hard part or above the film. The layer may be a film layer.

The cassette 1000 may be coupled to a blood treatment apparatus (not shown in FIG. 1) at least by its front side shown in FIG. 1. An exemplary technique for suitable coupling of a cassette 1000 to a coupling surface of a blood treatment apparatus is described in German Patent Application Nos. 10 2009 012 633.3 having the title "Vorrichtung zum Verbinden einer externen Funktionseinrichtung mit einer Anordnung, Anordnung aufweisend eine solche Vorrichtung und Verfahren zum Verbinden" [Device for connecting an external functional means to an arrangement, arrangement including a like apparatus, and connecting method] as filed with the German Patent and Trademark Office on Mar. 10, 2009, and 10 2009 012 632.5 having the title "Abdichtungseinrichtung zum Abdichten eines Volumens einer medizinischen Behandlungsanordnung gegen ein weiteres Volumen sowie Anordnung und Verfahren" [Sealing means for sealing a volume of a medical treatment arrangement against another volume, as well as arrangement and method] also filed with the German Patent and Trademark Office on Mar. 10, 2009, the respective disclosures of which are herewith fully incorporated by way of reference thereto.

The cassette 1000 may be coupled to a coupling surface of the blood treatment apparatus by the plane of the film 3 or through the intermediary of the latter. The coupling surface may preferably be realized three-dimensionally.

The coupling surface of the blood treatment apparatus may be inclined to the rear, for instance at an upper portion thereof shown in FIG. 1 by 8 degrees against a vertical line extending from top to bottom in FIG. 1 (in the direction extending from the observer into the plane of drawing in FIG. 1).

The cassette 1000 comprises an arterial patient connection 7.

The cassette 1000 further comprises an arterial pressure measurement chamber 9. The latter may include corresponding sensors. The sensors may transmit signals, preferably via cabling. The sensors may, however, alternatively or also be configured to transmit signals in a wireless manner.

The cassette 1000 comprises a connector 11 for the exit of blood from the cassette 1000 as well as a connector 13 for the entry of blood into the cassette 1000.

The two connectors 11 and 13 are adapted to be connected to a pump tube segment or pump tube set of a blood pump.

The cassette 1000 further comprises a chamber 15 including a pressure measurement site for pressure measurement in the extracorporeal blood circuit upstream from the dialyzer ("pre-filter") or downstream from the pump ("post-pump"), respectively.

At the chamber 15 the pressure in the extracorporeal circuit upstream from the dialyzer may be measured across the film 3 or via the film 3.

The cassette 1000 comprises an arterial filter conduit 17 as well as a venous filter conduit 19.

The interior of the cassette 1000 includes a venous blood chamber 21. The venous blood chamber 21 is subdivided into an upper space 23 and a lower space 25.

The upper space 23 of the venous blood chamber 21 may admit a laterally tangential inflow of blood. Here, blood may flow in laterally through the inlet (on the left side in FIG. 1) into the upper space 23 and spread out tangentially to the walls of the upper space 23. A laterally tangential inflow of blood may create a zone with a substantially or completely stable rotational flow of blood in the upper space 23 of the venous blood chamber 21.

The lower space 25 of the venous blood chamber 21 may represent a calming zone for the blood stream. Such a calming zone may possibly have substantially no rotational flow or no rotational flow of the blood present therein at all.

The venous blood chamber 21 is subdivided into the upper space 23 and the lower space 25 by a cross-sectional restriction 27 of the hard part 1 of the cassette 1000. The cross-sectional restriction 27 reduces the cross-section of the venous blood chamber 21 in its width and depth so as to result in a shoot or rapid, whereby a fluid having traversed the venous blood chamber 21 of the cassette 1000 will flow with slower flow velocity. The upper space 23 and the lower space 25 are in fluid communication.

By means of such a construction, i.e., a subdivision of the venous blood chamber 21 into a zone with substantially or completely stable rotational flow of the blood and a calming zone for the blood stream, it is advantageously possible to achieve an efficient separation of air from the blood or fluid.

Walls of the upper space 23 and of the lower space 25 of the venous blood chamber 21 may suitably be adapted to an inclination of the upper portion of the cassette 1000 in FIG. 1 against the vertical, for example a rearward inclination of the upper part of the cassette 1000 shown in FIG. 1 by 8 degrees (into the plane of drawing). It may suitably have a rounded shape so as to advantageously represent a rheologically optimized contact surface for fluids passing through the venous blood chamber 21.

The cassette 1000 comprises a clot trap 29.

As a clot trap, it is possible and preferable to use a clot trap as disclosed in German Patent Application No. 10 2009 024 495.6 having the title "Gerinnselfänger, externe Funktionseinrichtung, Blutkreislauf sowie Behandlungsvorrichtung" [Clot trap, external functional means, blood circuit and treatment apparatus] to the applicant of the present invention that was filed with the German Patent and Trademark Office on Jun. 10, 2009. The relevant disclosure thereof is herewith fully incorporated by way of reference thereto.

At the clot trap 29, it is possible to measure the pressure in the extracorporeal circuit through the film 3 or across the film 3, in particular after passage through the dialyzer.

The cassette 1000 comprises a venous patient connection 31.

The cassette 1000 further comprises an arterial heparin addition site 33. Here, it should be noted that the heparin addition site 33 (just like a venous heparin addition site 37) may also be suited and intended for adding other pharmacologically active agents than heparin, which are, only in a preferred manner, anti-coagulants or combinations of active agents. This should also be noted whenever heparin is mentioned previously or in the following in any kind of context.

The cassette 1000 comprises a check valve 35 of the arterial heparin addition site 33.

Exemplary check valves for the use as check valve 35 of the arterial heparin addition site 33 and also as further check valves of the cassette 1000 are disclosed in German Patent Application No. 10 2009 024 469.7 to the applicant of the present invention having the title "Ventilvorrichtung, Ventileinsatz, externe Funktionseinrichtung, Behandlungsvorrichtung sowie Verfahren" [Valve device, valve insert, external functional means, treatment apparatus, and method] as filed with the German Patent and Trademark Office on Jun. 10, 2009, and U.S. Provisional Patent Application No. 61/185,603, also filed on Jun. 10, 2009, the relevant disclosures of which are herewith fully incorporated by way of reference thereto.

The cassette 1000 comprises an arterial heparin addition valve 36. By means of the arterial heparin addition valve 36, the addition of heparin into the arterial filter conduit 17 may be controlled or regulated.

The arterial heparin addition valve 36 may be configured as a so-called phantom valve.

The expression "phantom valve" as presently used designates an element having an actor surface that may be reached by means of an actor (in the present case, for example, an actor membrane) that may adopt the function of a valve.

The actor membrane can be made to move, dilate or curve etc. in one direction by applying a force on it, e.g., a pressing force. As a result of its movement or dilatation, the actor membrane may come into contact with an element such as a sealing means, e.g. a bar, or move away from the latter. The actor membrane may thus, for example, effect or enhance or terminate or reduce a sealing effect.

When the force acting on the actor membrane is ceased to apply or is released, the latter may return, for example, to a basic position, e.g., a non-curved condition.

A phantom valve for use as an arterial heparin addition valve 36 as well as further phantom valves of the cassette 1000 may be configured with or from a bar portion of a passage at the hard part 1 of the cassette 1000 and a portion of the film 3 contacting or facing the bar portion.

Phantom valves may be operated through actors of the blood treatment apparatus.

In order to close a phantom valve, the portion of the film 3 may be pressed onto the bar portion. In order to open the phantom valve, the portion of the film 3 may again be raised from the bar portion.

Further examples and/or embodiments for phantom valves may be found in German Patent Application No. 10 2009 012 632.5 having the title "Abdichtungseinrichtung zum Abdichten eines Volumens einer medizinischen Behandlungsanordnung gegen ein weiteres Volumen sowie Anordnung und Verfahren" [Sealing means for sealing a volume of a medical treatment arrangement against another volume, as well as arrangement and method], as filed with the German Patent and Trademark Office on Mar. 10, 2009 by the present applicant. The relevant disclosure thereof is herewith fully incorporated by way of reference thereto.

The cassette 1000 comprises a venous heparin addition line or site 37. The venous heparin addition site 37 may be configured as a Luer-connector.

The cassette 1000 comprises a check valve 39 of the venous heparin addition site 37.

The cassette 1000 comprises a venous heparin addition valve 40. With the aid of the venous heparin addition valve 40, the addition of heparin into the venous filter conduit 19 may be controlled or regulated.

The cassette 1000 comprises a substituate addition site 41 or a substituate connector, respectively.

The substituate addition site 41 may be a connection means as described in German Patent Application No. 10 2009 024 575.8 to the present applicant having the title "Verbindungseinrichtung und Verfahren zum Verbinden wenigstens zweier fluidführender medizintechnischer Systeme, sowie medizintechnische Vorrichtung" [Connection means and method for connecting at least two fluid-conducting medical-technical systems, as well as a medical-technical apparatus] as filed with the German Patent and Trademark Office on Jun. 10, 2009, and U.S. Provisional Patent Application No. 61/185,687, also filed on Jun. 10, 2009. The relevant disclosures thereof are herewith fully incorporated by way of reference thereto.

The substituate addition site 41 may be provided with a touch-protection element (not shown). The substituate addition site 41 may be provided with a drip-protection element (not shown). The drip-protection element may be realized through an integrated closure sleeve. The drip-protection element may prevent residues of substituate and/or blood from dripping out when the cassette 1000 is released and subsequently removed from the blood treatment apparatus.

The drip-protection element may be provided as a removable element. Moreover, it may be configured as a hood or lid.

The substituate addition site 41 or some other portion of the cassette 1000 may moreover provide a tamper protection, as a result of which the user recognizes readily, or at one glance, whether the cassette 1000 has already been used. This tamper protection may be realized by means of the touch-protection element, the closure sleeve, and/or some other structure. Preferably, the corresponding structure may recognizably change its position inside or relative to the cassette 1000. Preferably it may change its shape.

Moreover, the substitute addition site 41 or some other portion of the cassette 1000 may provide a protection against reuse. In a preferred manner, the cassette 1000 is made unusable by means of a closure sleeve—preferably in an irreversible manner—with respect to an attempted reuse. If the cassette 1000 should nevertheless be used again, sensors of the blood treatment apparatus do not measure the signal characteristics that would be measured during use of a new cassette. This may be due to the fact that liquid can not enter into the cassette 1000 or into the substitute addition site 41, or at least not in a sufficient or usual quantity. The control unit of the blood treatment apparatus may recognize this. A warning may be triggered.

As a tamper protection or a protection against reuse, it is preferably possible to use a tamper protection or protection against reuse as disclosed by the applicant of the present invention in German Patent Application No. 10 2009 024 575.8 having the title "Verbindungseinrichtung und Verfahren zum Verbinden wenigstens zweier fluidführender medizintechnischer Systeme, sowie medizintechnische Vorrichtung" [Connection means and method for connecting at least two fluid-conducting medical-technical systems, as well as a medical-technical apparatus] that was filed with the German Patent and Trademark Office on Jun. 10, 2009, and U.S. Provisional Patent Application No. 61/185,687, also filed on Jun. 10, 2009. The relevant disclosures thereof are herewith fully incorporated by way of reference thereto.

The cassette comprises a connector 43 for the exit of substitute from the cassette 1000 as well as a connector 45 for the entry of substitute into the cassette 1000.

The connectors 43 and 45 are adapted to be connected to a pump tube segment or a pump tube set of a substitute pump.

The cassette 1000 comprises a check valve 47 for the addition of substitute. Substitute may be introduced into a substitute conduit 49 by operating the check valve 47.

The cassette 1000 comprises a pre-dilution addition valve 51. The pre-dilution addition valve 51 may be configured as a phantom valve.

The cassette 1000 comprises a post-dilution addition valve 53. The post-dilution addition valve 53 may be configured as a phantom valve.

The cassette 1000 comprises a single-needle sterile membrane 55.

The cassette 1000 comprises a single-needle chamber 57. In FIG. 1, the single-needle chamber 57 is disposed above the venous blood chamber 21.

Inside the single-needle chamber 57 a blood surge redirection element 59 is arranged. The blood surge redirection element 59 may serve for decelerating a blood surge and/or cancelling its impulse.

A connection to an inside of the single-needle chamber 57 may be provided by means of connection means as disclosed by the applicant of the present invention in German Patent Application No. 10 2009 024 467.0 having the title "Einrichtung sowie externe Funktionseinrichtung and Behandlungsvorrichtung zum Behandeln von medizinischen Fluiden" [Device and external functional means and treatment apparatus for the treatment of medical fluids] that was filed with the German Patent and Trademark Office on Jun. 10, 2009, and U.S. Provisional Patent Application No. 61/185, 604, also filed on Jun. 10, 2009. The relevant disclosures thereof are herewith fully incorporated by way of reference thereto.

The cassette 1000 comprises a single-needle blood valve 61. The single-needle blood valve 61 may be configured as a phantom valve.

The cassette 1000 comprises an evacuation site 63. The evacuation site 63 may serve for vacuum coupling of the cassette 1000 to the blood treatment apparatus as is described, for example, in German Patent Application No. 10 2007 042 964 A1 having the title "Vorrichtung and Verfahren zur Behandlung einer medizinischen Flüssigkeit" [Apparatus and method for treating a medical liquid] that was filed with the German Patent and Trademark Office on Sep. 10, 2007, the relevant disclosure of which is herewith fully incorporated by way of reference thereto.

The cassette 1000 comprises a primary alignment center 65. The primary alignment site or center 65 may advantageously serve for aligning and/or latching of the cassette 1000 on the blood treatment apparatus.

The cassette 1000 comprises a secondary alignment center or site 67. The secondary alignment site 67 may serve for aligning and/or latching of the cassette 1000 on the blood treatment apparatus.

Figure 4:
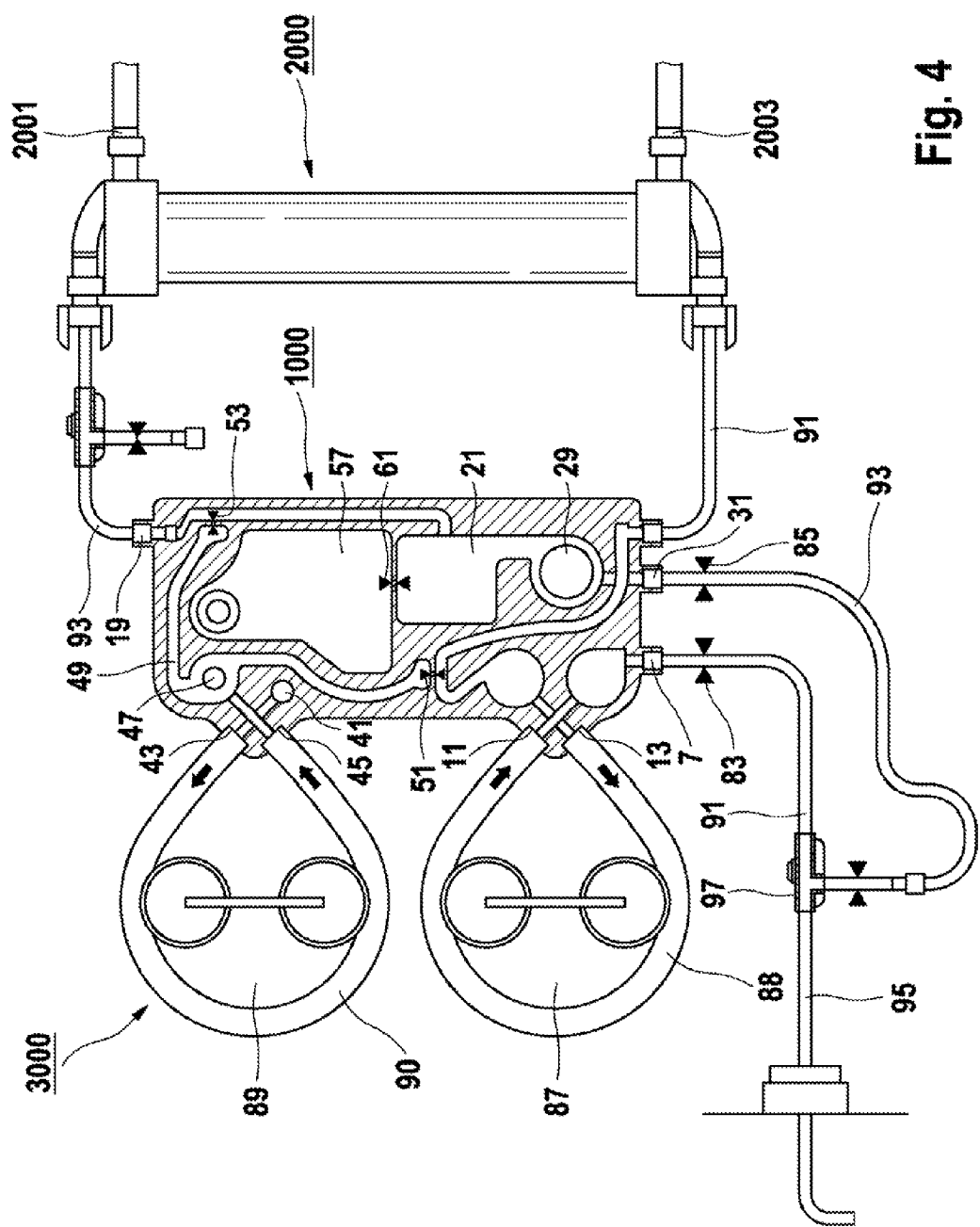
FIG. 4 shows in a simplified schematic representation a phase during the performance of a preparatory or priming process in accordance with the invention prior to performing a blood treatment process.

The cassette 1000 is filled with gas (e.g., sterile air) prior to beginning priming. During priming of the extracorporeal blood circuit, this gas filling has to be displaced. Insofar, a blood treatment cassette generally represents a particular challenge as there are both rising and falling conduits and moreover chambers in which no "air nests" must remain. For this purpose, the present cassette 1000 is provided with special construction features:

The chamber 15 for measuring the arterial pressure is constructed such that the entire air volume may rise into a pump tube segment (e.g., into the pump tube segment 90; see, e.g., FIG. 4). Advantageously, there are no dead spaces present. Air rising by itself from the arterial pressure measurement chamber into the pump tube segment of the blood pump is forcibly conveyed through the pump tube segment from the engagement range of the blood pump (e.g., by the rollers of a roller pump). As soon as the pump ceases to exert an influence (for instance due to disengaging rollers), the air rises by itself into the cassette 1000 in the conveying direction.

The venous recirculation conduit (or a venous portion 93 of the extracorporeal circuit as shown, inter alia, in FIG. 4) is a downward conduit. Starting from a particular volume flow (e.g., 200 ml/min in the case of the cassette 1000 shown in FIG. 1), air bubbles in the blood are "entrained" even against gravitational acceleration. This effect is utilized in the downward conduits. The conduit cross-sections of the downward conduits are designed with such a small size that a forcible conveyance of the air bubbles even against gravitational acceleration is successful due to the flow velocity.

In the venous blood chamber 21, large cross-sections are provided, such that air bubbles may reliably rise there against the main direction of flow due to the slower or lower flow velocities present in this location.

Further constructive features of the cassette 1000 are as follows:

The phantom valves 40, 51 and 53 are physically oriented such that blood (which has a higher density than water or substitute etc.) has difficulty or is unable to penetrate "upward" or "sideways" into opened phantom valves while the cassette 1000 is operated with blood, for the latter descends as compared to the lighter water. Such an advantageous orientation is realized with the aid of the phantom valves 40, 51, and 53. The valve 36, on the other hand, does not have such a requirement, i.e., the orientation is not crucial there.

For the same reason, the conduit passage (stub passage) below the check valve 47 for adding substituate is constructed in a rising manner. In the event of a malfunction of the pre- and/or post-dilution valves 51 and 53 and a resulting bypass flow of blood, blood cannot rise into the substituate conduit 49 any more. Rather, the blood will flow past the opening of the corresponding stub conduit.

The inclination of the cassette 1000 preferably is from 5 degrees to 11 degrees, and in a particularly preferred arrangement, the 8 degrees already mentioned above.

Figure 2:
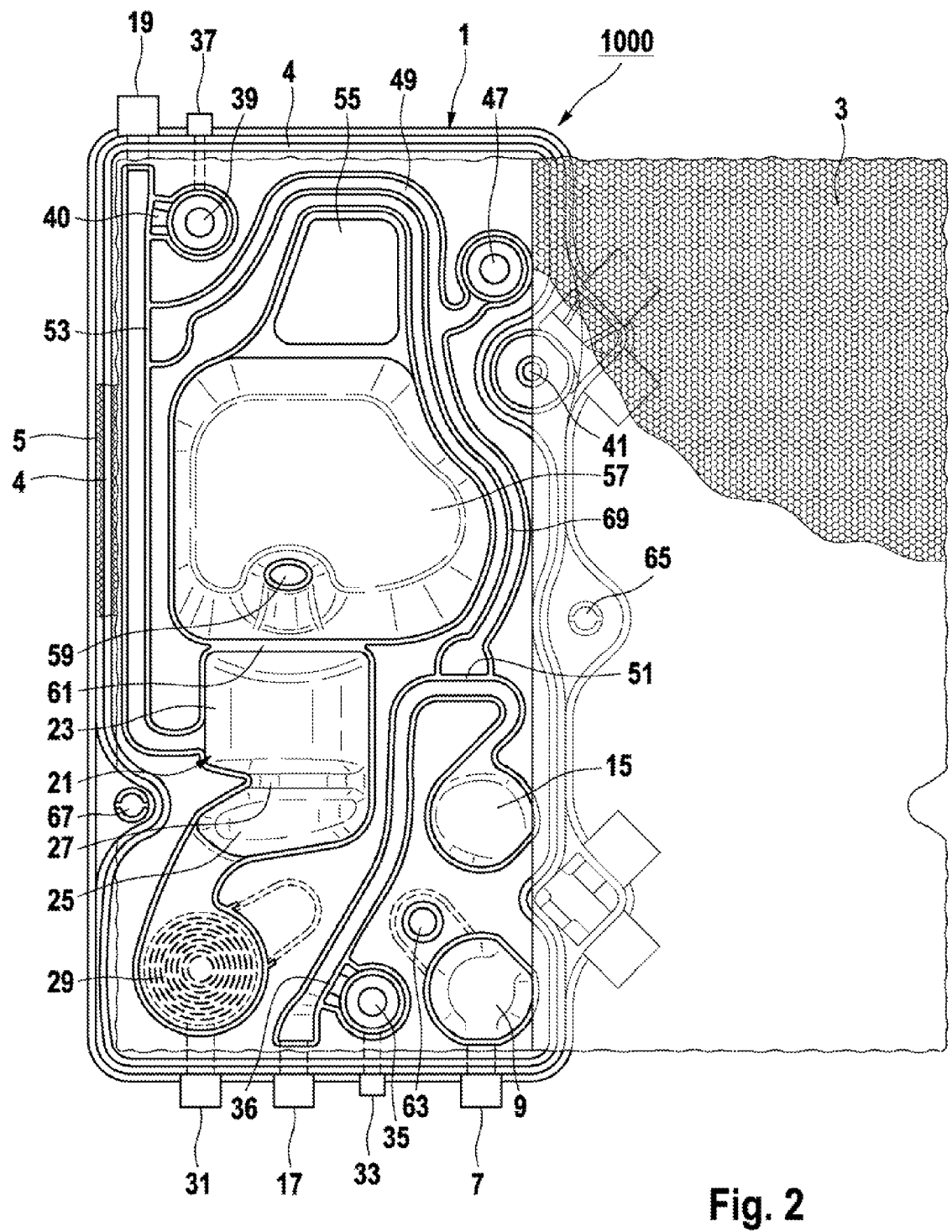
FIG. 2 shows the external functional means of FIG. 1 with the cover means swung open following destructive cutting.

FIG. 2 shows the cassette 1000 of FIG. 1, wherein the film 3 may be seen to be cut open destructively at the left-hand margin of the cassette 1000 as well as at the top and bottom and swung open to the right for better illustration.

As is shown in FIG. 2, the film 3 has a surface texture.

FIG. 2 shows the elements inside the cassette 1000 which are visible in more detail after having cut open the film 3.

In order to avoid repetitions, reference is made to the configurations of the individual elements discussed in the description of FIG. 1.

Here it is clearly seen that the cassette 1000 comprises a sealing bar 69. The sealing bar 69 may be employed, for instance, for forming or realizing the pre-dilution addition valve 51.

Figure 3:
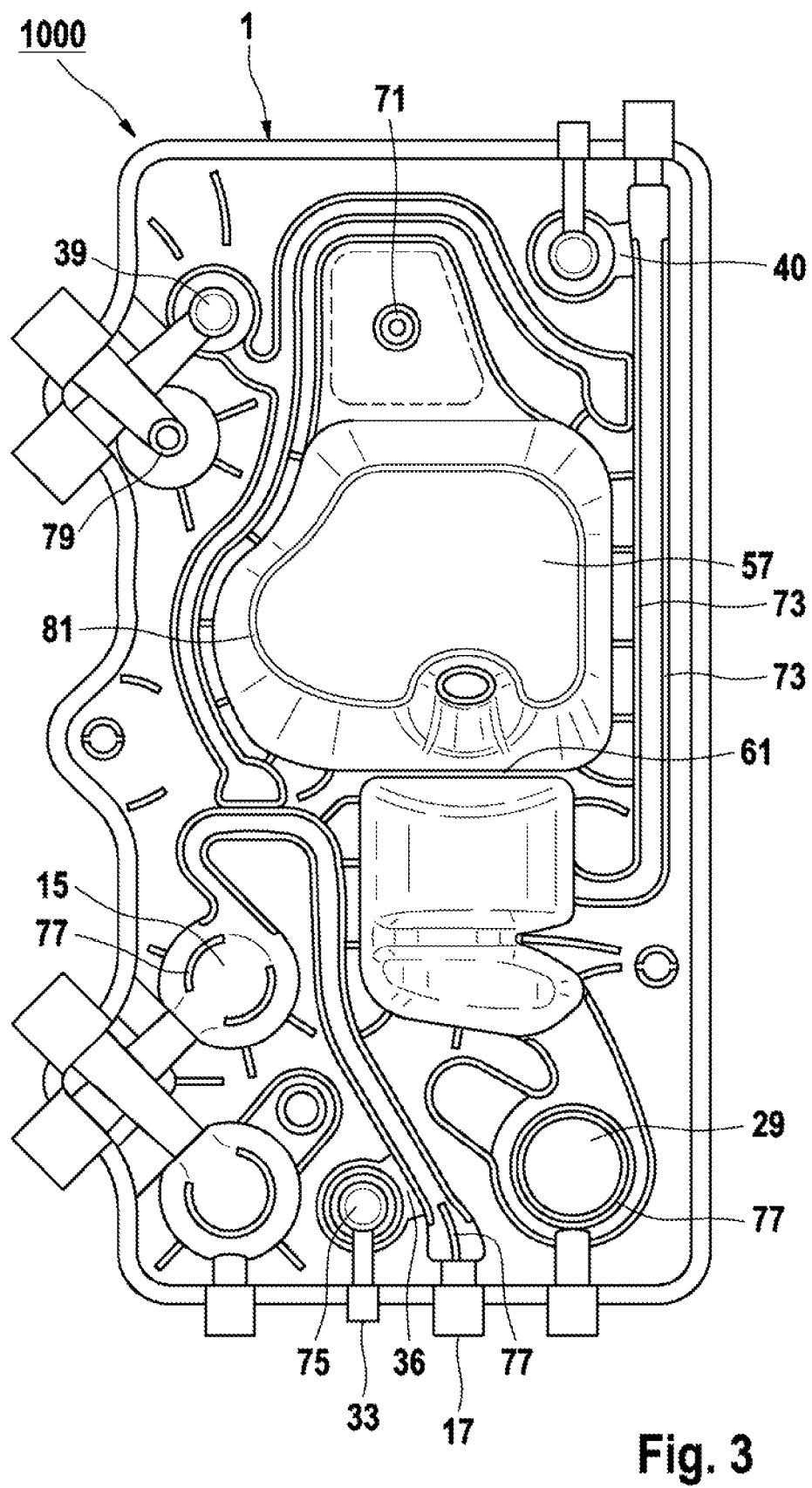
FIG. 3 shows the external functional means of FIG. 1 and FIG. 2 from its rear side.

FIG. 3 shows the cassette 1000 from its rear side. When the cassette 1000 is coupled to the blood treatment apparatus, an observer opening a door of the blood treatment apparatus for removing the cassette 1000 will look upon this rear side.

The cassette 1000 comprises a single-needle air connector 71. A support grid (not shown) of the single-needle sterile membrane 55 may be provided or arranged at the single-needle air connector 71 on the apparatus side and/or on the blood side.

The cassette 1000 comprises several support bars. The support bars have different heights relative, e.g., to the plane of the film 3. The support bars are projected in the side of the cassette 1000 facing the observer in FIG. 3, i.e., out of the plane of drawing of FIG. 3.

The cassette 1000 comprises support bars 73 having a height of 5 mm, support bars 75 having a height of 8 mm, support bars 77 having a height of 13 mm, support bars 79 having a height of 24 mm, and support bars 81 having a height of 31 mm. These and other numeric values should, of course, be understood to be non-limiting examples.

The support bars may serve to support the cassette, in the state of being coupled to a blood treatment apparatus, against a lid of a reception means of the blood treatment apparatus for receiving the cassette. Exemplary embodiments of such a coupling of the cassette to the blood treatment apparatus are given in German Patent Application No. 10 2009 012 633.3 having the title "Vorrichtung zum Verbinden einer externen Funktionseinrichtung mit einer Anordnung, Anordnung aufweisend eine solche Vorrichtung and Verfahren zum Verbinden" [Device for connecting an external functional means to an arrangement, arrangement including a like apparatus, and connecting method] as filed with the German Patent and Trademark Office on Mar. 10, 2009, the relevant disclosure of which is herewith fully incorporated by way of reference thereto.

In FIG. 3 the cassette 1000 is shown as it will be viewed by the user/observer after its coupling to the machine interface. The inclination of the cassette 1000 relative to the machine is realized with a "rearward inclination", so that the upper edge is located at a further distance from the user/observer than the lower edge.

The upwardly facing surfaces of the venous blood chamber 21 and of the single-needle chamber 57 accordingly have such an inclination that air bubbles may still reliably rise on the inside despite the inclination of the cassette 1000. As an alternative, a cassette design which does not provide any inclination of the cassette is, of course, basically also possible.

In the following, different processes in accordance with the invention that may be employed using the external functional means of the invention in blood treatment methods shall be described by making reference to FIGS. 4 to 16.

The blood treatment apparatus comprises an external functional means, for instance the cassette 1000 as discussed in FIGS. 1 to 3 and having the elements previously described in FIGS. 1 to 3.

The blood treatment apparatus further comprises a dialyzer or dialyzing means 2000 having a dialyzing liquid inlet 2001 and a dialyzing liquid outlet 2003.

The blood treatment apparatus moreover comprises an extracorporeal circuit 3000.

The extracorporeal circuit 3000 comprises an arterial patient tube clamp 83 and a venous patient tube clamp 85.

The extracorporeal circuit 3000 comprises a blood pump 87 having a pump tube segment 88.

The extracorporeal circuit 3000 comprises a substituate pump 89 having a pump tube segment 90.

The blood pump 87 and the substituate pump 89 may be configured as peristaltic pumps, for example roller pumps as shown in the figures.

The expression "conveying direction" or "direction of flow" designates the usual conveying directions during a blood treatment, i.e., of the blood to be purified from a patient to a dialyzer or dialyzing means, and of the purified blood from the dialyzer or dialyzing means back into the patient. In the plane of drawing of the figure, this conveying direction is in the counter-clockwise direction.

Likewise, the expressions "conveying direction" or "direction of flow" in connection with the flow of a substituate designate a usual conveying direction of the substituate during a blood treatment from the substituate addition valve 41 into the extracorporeal circuit 3000.

A conveyance of fluid (in particular blood and substituate) taking place against this conveying direction is designated as conveyance or flow in the opposite direction.

The extracorporeal circuit 3000 comprises an arterial portion 91 and a venous portion 93.

The arterial portion 91 of the extracorporeal circuit 3000 extends from a portion for arterial connection of a patient, for instance an arterial needle, through the cassette 1000 towards a blood inlet at the dialyzing means 2000. The arterial portion 91 has various components. Thus, an arterial connection of a patient, the arterial patient connection 7, the arterial patient tube clamp 83, the arterial pressure measurement chamber 9, the chamber 15 with an arterial post- or pre-filter pressure measurement site, the pump tube segment 88 of the blood pump 87, the arterial filter conduit 17, and a blood inlet at the dialyzing means 2000 are all part of the arterial portion 91 of the extracorporeal circuit 3000.

The venous portion 93 of the extracorporeal circuit 3000 extends from a blood outlet at the dialyzing means 2000 towards a portion for venous connection of a patient, for instance a venous needle. The venous portion 93 has various components. Thus, a blood outlet from the dialyzer or dialyzing means 2000, the venous filter conduit 19, the venous blood chamber 21, the clot trap 29, the single-needle chamber 57, the venous patient connection 31, the venous patient tube clamp 85, and a venous connection of a patient are all part of the venous portion 93 of the extracorporeal circuit 3000.

FIG. 4 shows a phase during the performance of a preparatory process or priming process for filling the utilized fluid conduits in accordance with the method of the invention.

The arterial portion 91 and the venous portion 93 of the extracorporeal circuit 3000 are connected to each other.

The pre-dilution addition valve 51, the post-dilution addition valve 53, and the single-needle blood valve 61 of the cassette 1000 are opened. The two patient tube clamps 83 and 85 are also opened.

FIG. 4 shows the described configuration as a momentary state or a phase during the preparatory or priming process.

Substituate is introduced into the extracorporeal circuit 3000 via the substituate addition site 41. To this end, the automatic substituate connector is connected. The arterial patient tube in the arterial portion 91 of the extracorporeal circuit 3000 and the venous patient tube in the venous portion 93 of the extracorporeal circuit 3000 are connected to a rinse port of the blood treatment apparatus, e.g., by means of a suitable connector providing an appropriate access from one end of the one patient tube to the other patient tube. The end of the other patient tube serves as a drain conduit into the rinse port. The connector may alternatively be situated in the arterial or venous patient conduit, i.e., the arterial portion 91 or the venous portion 93.

The venous patient tube clamp 85 is closed, the post-dilution addition valve 53 is opened, the pre-dilution addition valve 51 is closed.

Filling the venous blood chamber 21 is carried out by means of the substituate pump 89 through the post-dilution addition valve 53. Here, a separation of air takes place through the single-needle blood valve 61.

The blood pump 87 operates in a forward direction and aspires or sucks in substituate from the venous blood chamber 21.

When the level in the venous blood chamber 21 drops, replenishing via the post-dilution addition valve 53 is performed until the level detector recognizes that the predetermined filling level is exceeded. During this process, which is repeated according to need, continuous operation of the blood pump is maintained.

The clot trap 29 is de-aerated "from below": All three cassette valves (51, 53, 61) are closed. The arterial patient tube clamp 83 is opened, and the venous patient tube clamp 85 is closed. The rinse port is closed.

The blood pump 87 operates in the reverse direction for a short time to convey a small volume. Hereby, a venous negative pressure and an arterial overpressure are generated in the extracorporeal circuit 3000.

The venous patient tube clamp 85 is opened for as long as the a pressure equilibrium is established.

Subsequently, filling of the extracorporeal circuit 3000 is continued.

By means of the sensor/detector 115 at the venous patient tube clamp 85, e.g., a venous air bubble detector, the occurrence of air bubbles is detected. As soon as no air bubbles or nearly no air bubbles are detected in the course of a predetermined time interval, the extracorporeal circuit 3000 is assumed to be filled.

Then the filled extracorporeal circuit 3000 is rinsed. During rinsing, substituate is conveyed through the pre-dilution addition valve 51 and discarded through the rinse port ("plug valve 97").

In the process, both the arterial patient tube clamp 83 and the venous patient tube clamp 85 are opened. The blood pump 87 operates in the reverse direction and conveys a part of the substituate into the rinse port.

As was already mentioned in the foregoing, as an alternative for on-line filling (where the substituate is supplied on-line in the dialysis machine), it is also possible to perform filling with an external bag containing saline solution as a source for filling liquid. To this end, the arterial patient conduit or the arterial portion 91 of the extracorporeal circuit 3000 is coupled to the bag containing saline solution. The venous patient conduit or the venous portion 93 of the extracorporeal circuit 3000 is coupled to a so-called waste bag as a sink for the used saline solution. The blood pump 87 operates in the forward direction. By opening the pre-dilution addition valve 51 and the post-dilution addition valve 53, it is also possible to fill the conduit situated between these two valves.

In both methods, the patient is coupled to the extracorporeal circuit 3000 not before a predetermined rinsing quantity has been reached.

Figure 5:
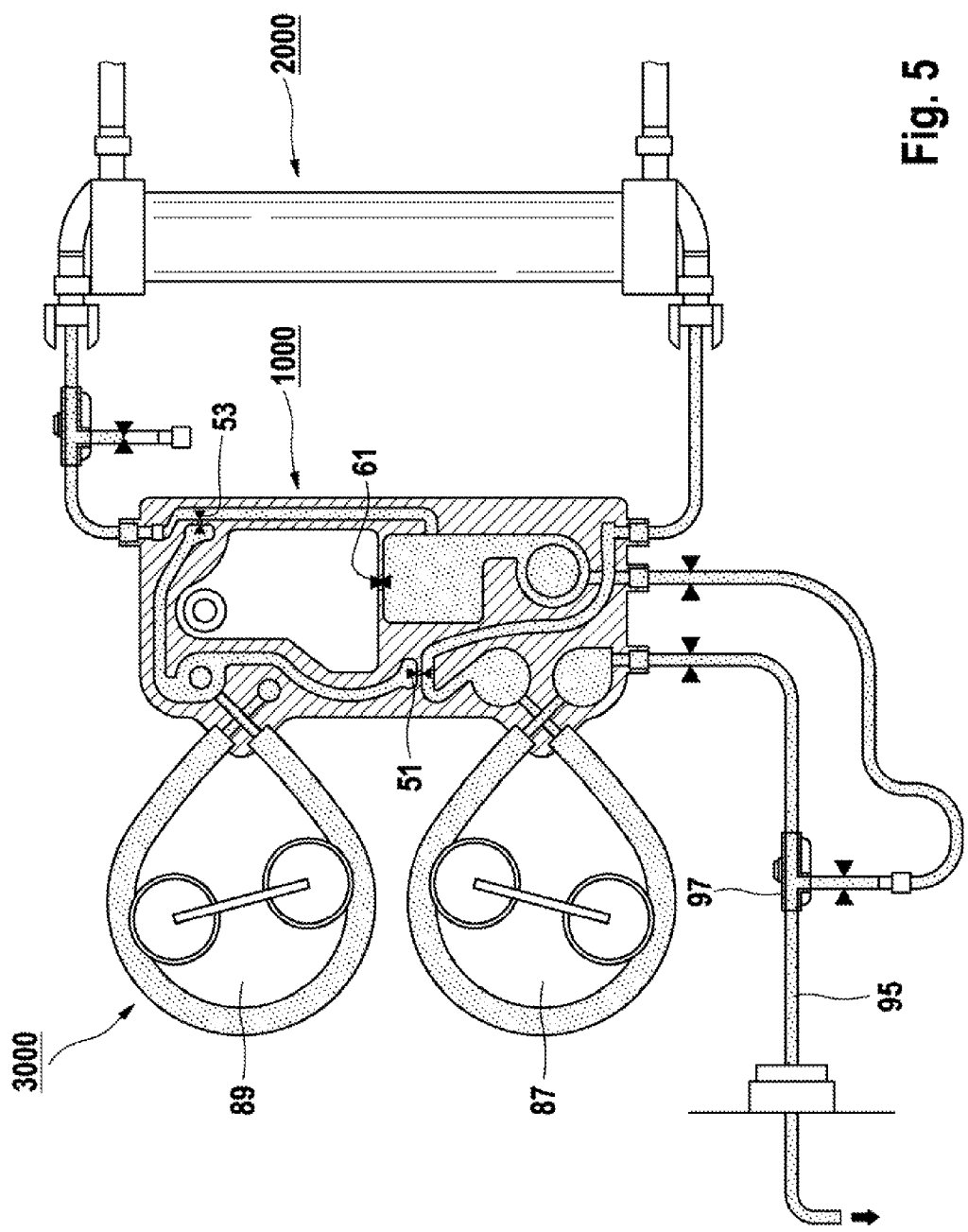
FIG. 5 shows in a simplified schematic representation a phase during the performance of a rinsing-process in accordance with the invention prior to performing a blood treatment process.

FIG. 5 shows a phase of a rinsing process in accordance with the method of the invention.

In order to remove the substituate circulating in the extracorporeal circuit 3000 (which is now closed) from the latter after preparation or filling (priming), the plug valve 97 is opened.

The substituate pump 89 is activated again. The pre-dilution addition valve 51 is opened.

The blood pump 87 and the substituate pump 89 convey the substituate out of the extracorporeal circuit 3000 via the drain conduit 95.

FIG. 5 shows the described configuration as a momentary state or in a phase of the rinsing process.

The blood pump 87 and the substituate pump 89 constantly convey new substituate, so that the extracorporeal circuit 3000 is rinsed. The substituate used is discarded.

The blood pump 87 and the substituate pump 89 each convey in the clockwise direction. The blood pump 87 and the substituate pump 89 may convey at an offset from each other. The substituate pump 89 may rotate more rapidly than the blood pump 87.

Figure 6:
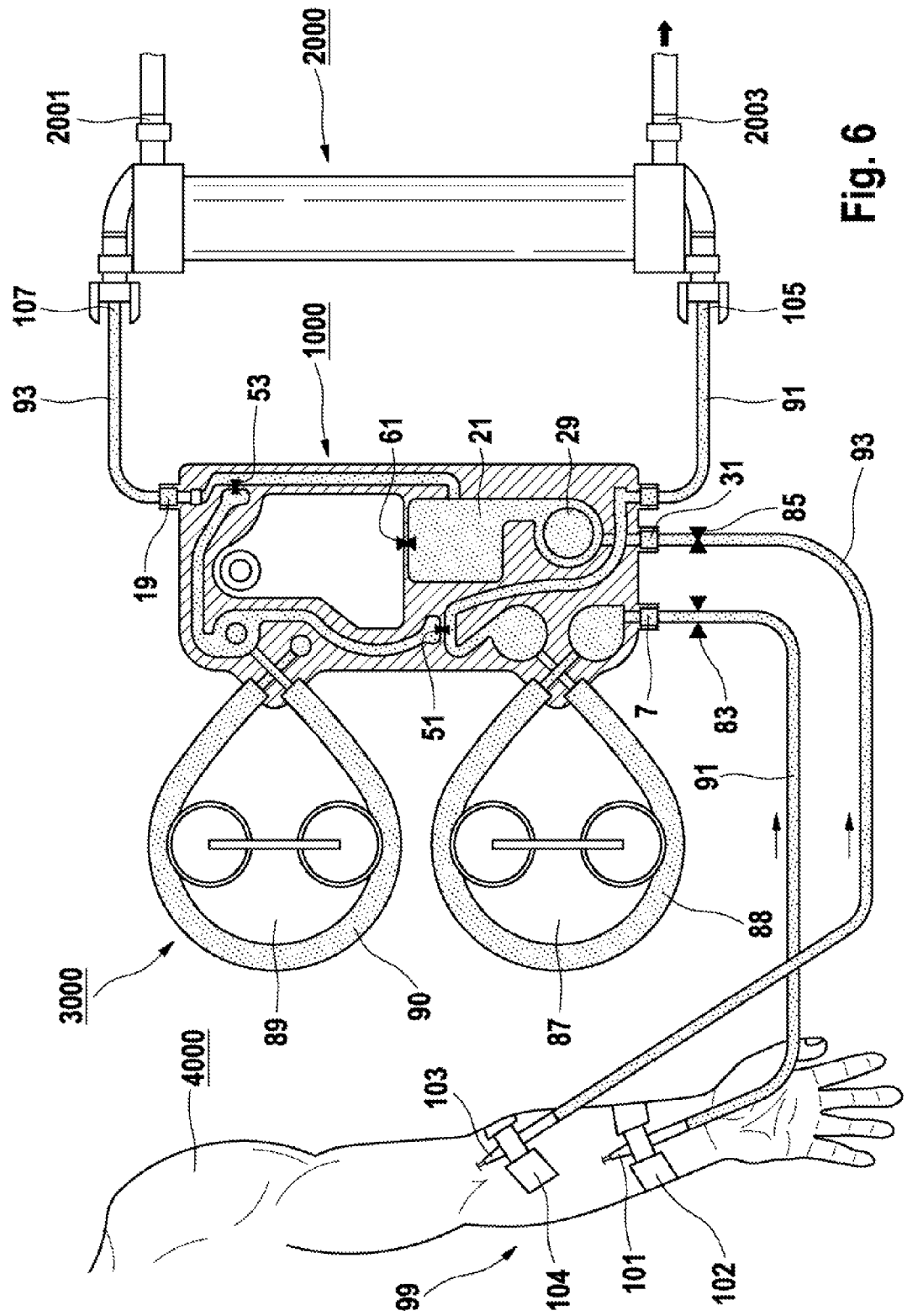
FIG. 6 shows in a simplified schematic representation a phase during the performance of a first process in accordance with the invention for connecting a patient to an extracorporeal circuit of a blood treatment apparatus.

FIG. 6 shows a phase during connecting a patient 4000 to the extracorporeal circuit 3000 in accordance with the method of the invention in a first manner by means of a double-needle access 99. As all figures presenting method steps, FIG. 6 also only represents one phase.

In order to couple a patient 4000 to the blood treatment apparatus, a double-needle access 99 is used.

The double-needle access 99 comprises an arterial needle 101 having a fixation 102, e.g., a sleeve, tape and the like, and a venous needle 103 having a fixation 104, e.g., a sleeve, tape and the like.

The arterial needle 101 is connected to the arterial patient connection 7 of the cassette 1000. The venous needle 103 is connected to the venous patient connection 31 of the cassette.

The venous needle 103 is placed on the patient 4000 and immobilized or fixed. The arterial needle 101 is placed on the patient 4000 and fixed. The venous needle 103 may be connected to the patient 4000 before the arterial needle 101.

As a result of filling, the extracorporeal circuit 3000 is filled with substituate. The pre-dilution addition valve 51, the post-dilution addition valve 53, and the single-needle blood valve 61 are closed.

Initially both patient tube clamps 83 and 85 are closed.

The blood pump 87 is activated. The arterial patient tube clamp 83 is opened.

FIG. 6 shows the described configuration as a momentary state with the arterial patient tube clamp 83 already opened, shortly before starting the blood pump 87.

Blood is conveyed from the patient 4000 via the arterial needle 101 into the arterial portion 91 of the extracorporeal circuit 3000 and displaces or conveys the substitute. The substitute is conveyed out of the blood treatment apparatus via the dialyzing liquid outlet 2003 of the dialyzing means 2000.

When the blood from the arterial portion 91 of the extracorporeal circuit 3000 arrives at a blood inlet 105 at the dialyzer or dialyzing means 2000, the arterial patient tube clamp 83 is closed and the blood pump 87 is stopped.

The venous patient tube clamp 85 is opened.

Blood enters into the venous portion 93 of the extracorporeal circuit 3000 in the opposite direction via the venous needle 103. The blood pump 87 is not activated.

The blood may, for example, enter the venous portion 93 on account of gravity.

The blood flows in the opposite direction through the venous portion 93 and enters the clot trap 29 and the venous blood chamber 21. The blood flows through the venous filter conduit 19 and enters the dialyzing means 2000 through the blood outlet 107 in the opposite direction.

Figure 7:
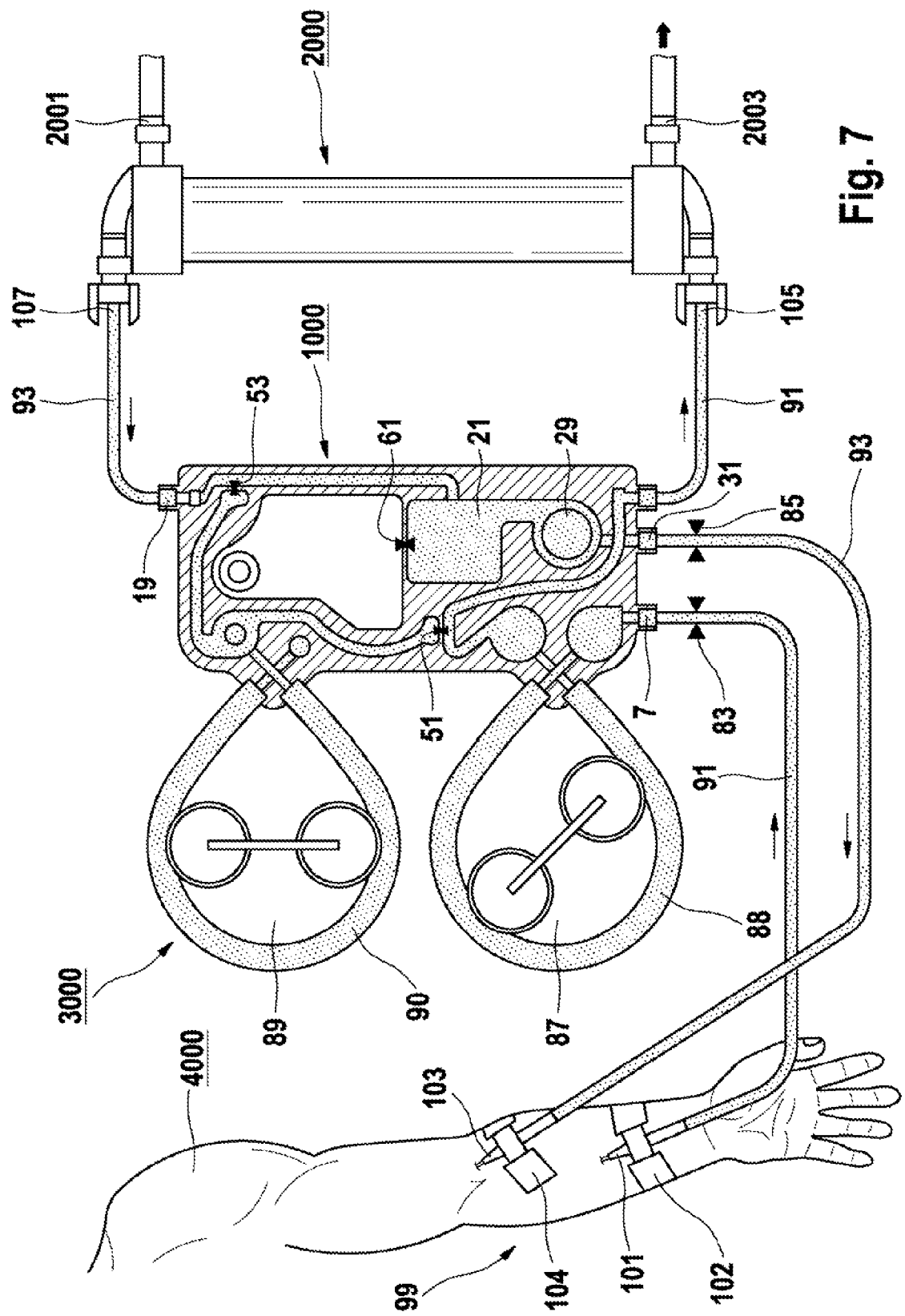
FIG. 7 shows in a simplified schematic representation a phase during the performance of a second process in accordance with the invention for connecting a patient to an extracorporeal circuit of a blood treatment apparatus.

FIG. 7 illustrates a phase of a second mode or of an alternative process for connecting a patient 4000 to a blood treatment apparatus.

The patient 4000 is connected to the extracorporeal circuit 3000 by means of an arterial needle 101 and a venous needle 103.

The arterial patient tube clamp 83 and the venous patient tube clamp 85 are opened. The pre-dilution addition valve 51, the post-dilution addition valve 53, and the single-needle blood valve 61 are closed.

Substitute is present in the entire extracorporeal circuit 3000 (except in the single-needle chamber 57).

The blood pump 87 is started. The dialyzing means 2000 at this stage is not turned on.

FIG. 7 shows the described configuration as a momentary state. At this time, nothing but substitute is present in the extracorporeal circuit 3000.

By operating the blood pump 87, blood is conveyed out of the patient 4000 through the arterial needle 101 into the arterial portion 91 of the extracorporeal circuit 3000. The blood flows into the dialyzing means 2000 at the blood inlet 105 thereof, and from there through the blood outlet 107 of the dialyzing means 2000 into the venous portion 93 of the extracorporeal circuit 3000.

The blood arrives in the cassette 1000 via the venous filter conduit 19 and enters into the venous blood chamber 21 in the closed position of the post-dilution addition valve 53, wherein the blood may flow tangentially into the upper space of the venous blood chamber 21.

From the venous blood chamber 21 the blood leaves the cassette 1000 via the clot trap 29 to arrive back at the patient 4000 via the venous patient connection 103.

Figure 8:
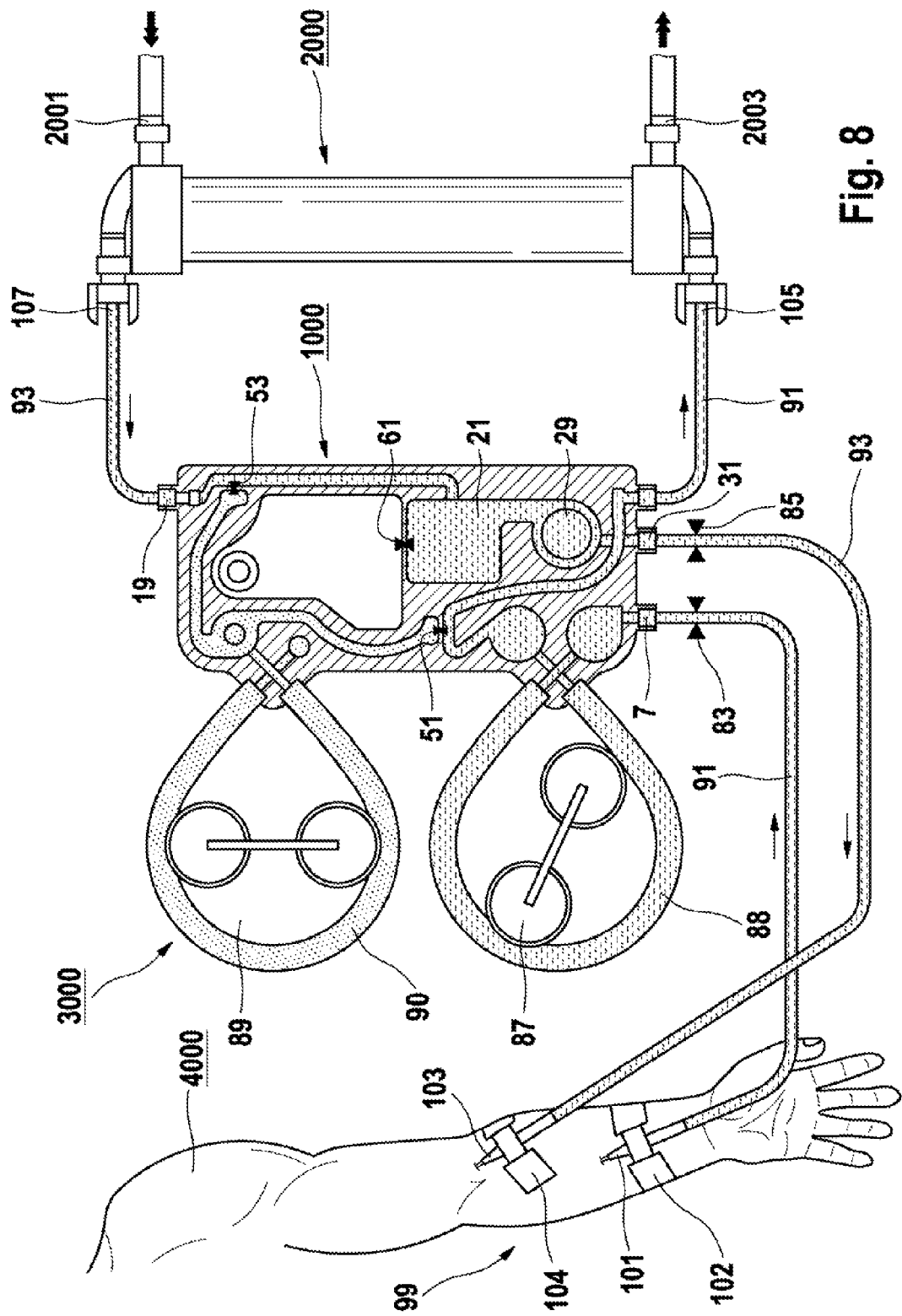
FIG. 8 shows in a simplified schematic representation a phase during the performance of a first blood treatment process in accordance with the invention.

FIG. 8 shows a phase of a dialysis treatment using a double-needle access to the patient.

The arterial patient tube clamp 83 and the venous patient tube clamp 85 are opened. The pre-dilution addition valve 51, the post-dilution addition valve 53, and the single-needle blood valve 61 are closed.

FIG. 8 shows the described configuration as a momentary state during a dialysis treatment under operation of the blood pump 87.

The dialyzing means 2000 is operated, so that dialyzing liquid enters into the dialyzing means 2000 at the dialyzing liquid inlet 2001. In the dialyzing means the treatment of the patient's blood is performed. The dialyzing liquid exits from the dialyzing means 2000 at the dialyzing liquid outlet 2003. Spent dialyzing liquid may be discarded or purified.

The blood pump 87 conveys blood from the patient 4000 via the arterial needle 101 into the arterial portion 91 of the extracorporeal circuit 3000, with the blood passing through the cassette 1000 and being conveyed to the dialyzing means 2000.

The blood flows through the dialyzing means 2000 in the opposite direction to the dialyzing liquid and is purified in the process. At the blood outlet 107 of the dialyzing means 2000, the purified blood leaves the dialyzing means 2000 and flows through the venous filter conduit 19 into the cassette 1000, enters the venous blood chamber 21 and the clot trap 29, and exits from the cassette 1000 at the venous patient connection 31.

The purified blood is again returned into the patient 4000 via the venous patient connection 103.

Feeding of substitute does not take place at this stage. The substitute pump 89 at this stage is not operated.

Figure 9:
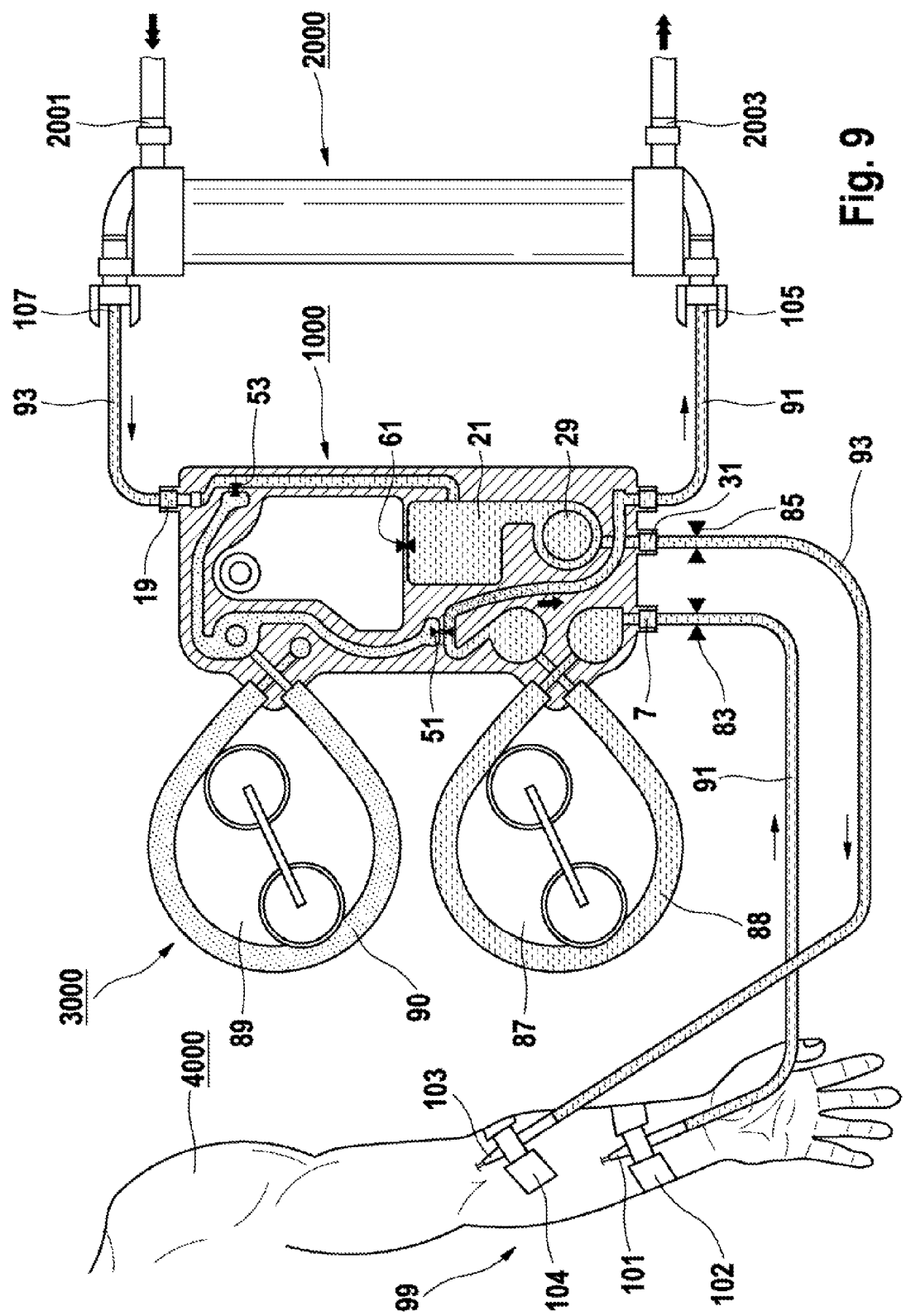
FIG. 9 shows in a simplified schematic representation a phase during the performance of the blood treatment process of FIG. 8 by using pre-dilution.

FIG. 9 shows a phase of the blood treatment process represented through FIG. 8 by using a pre-dilution of the blood with substitute ("on-line HDF pre-dilution").

The pre-dilution addition valve 51 is opened. The post-dilution addition valve 53 and the single-needle blood valve 61 are closed. The blood pump 87 is operated. The substitute pump 89 is started. The substitute pump 89 may be operated in synchronicity with the blood pump 87.

The described configuration is represented in FIG. 9 as a momentary state, with substitute being present between pre-dilution addition valve 51 and post-dilution addition valve 53 and blood flowing through the remaining extracorporeal circuit 3000.

The substitute pump 89 conveys substitute which enters the arterial portion 91 of the extracorporeal circuit 3000 at the pre-dilution addition valve 51 and mixes up with the blood in order to be purified.

Figure 10:
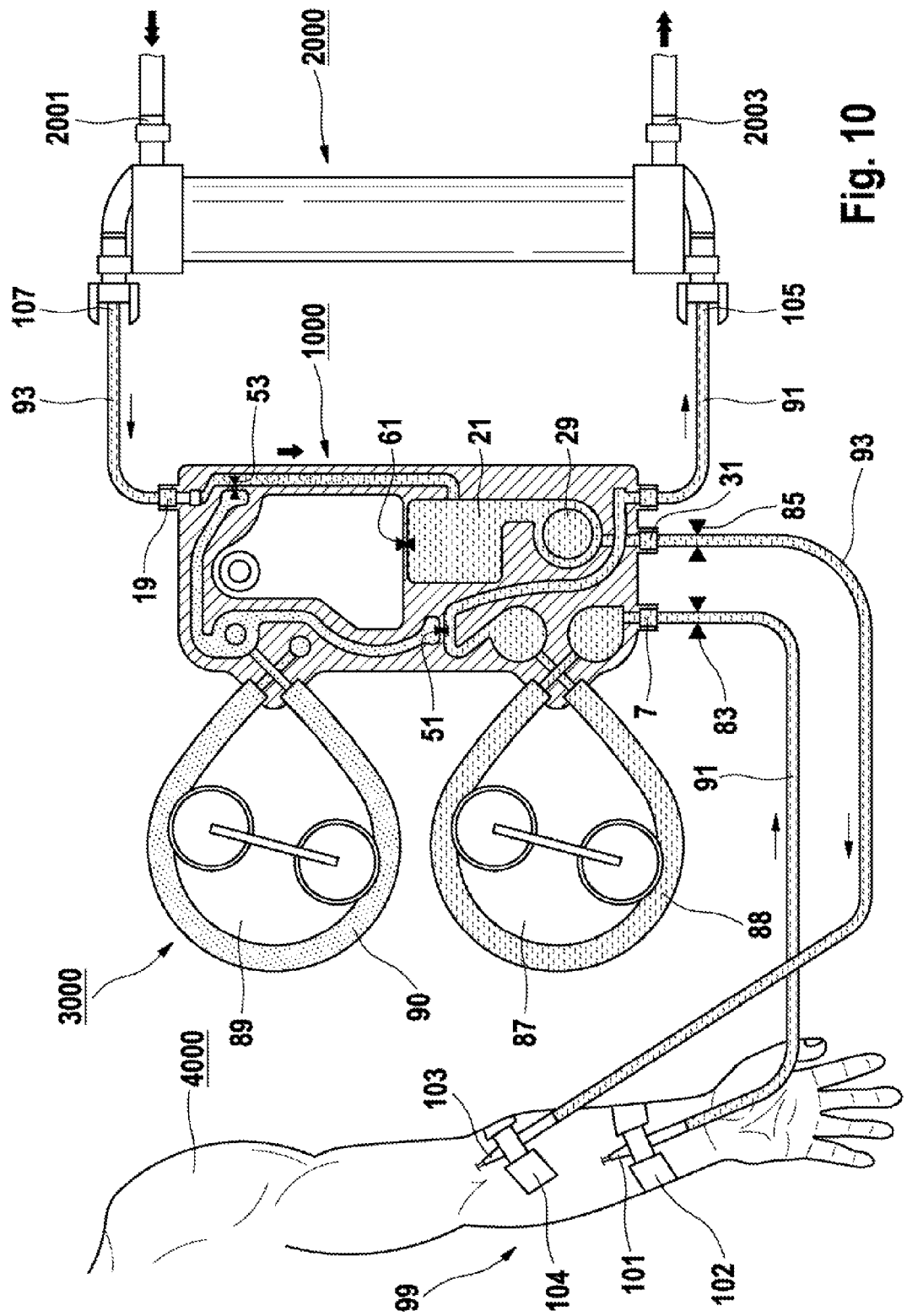
FIG. 10 shows in a simplified schematic representation a phase during the performance of the blood treatment process in accordance with the invention of FIG. 8 by using post-dilution.

FIG. 10 shows a phase of the blood treatment process represented in FIG. 8 by using a post-dilution of the blood with substitute ("on-line HDF post-dilution").

The post-dilution addition valve 53 is opened. The pre-dilution addition valve 51 and the single-needle blood valve 61 are closed. The blood pump 87 is operated. The substitute pump 89 is started. The substitute pump 89 may be operated in synchronicity with the blood pump 87.

The described configuration is represented in FIG. 10 as a momentary state, with substitute being present between pre-dilution addition valve 51 and post-dilution addition valve 53 and blood flowing through the remaining extracorporeal circuit 3000.

The substitute pump 89 conveys substitute which enters the venous portion 93 of the extracorporeal circuit 3000 at the post-dilution addition valve 53 and mixes up with the purified blood.

Figure 11:
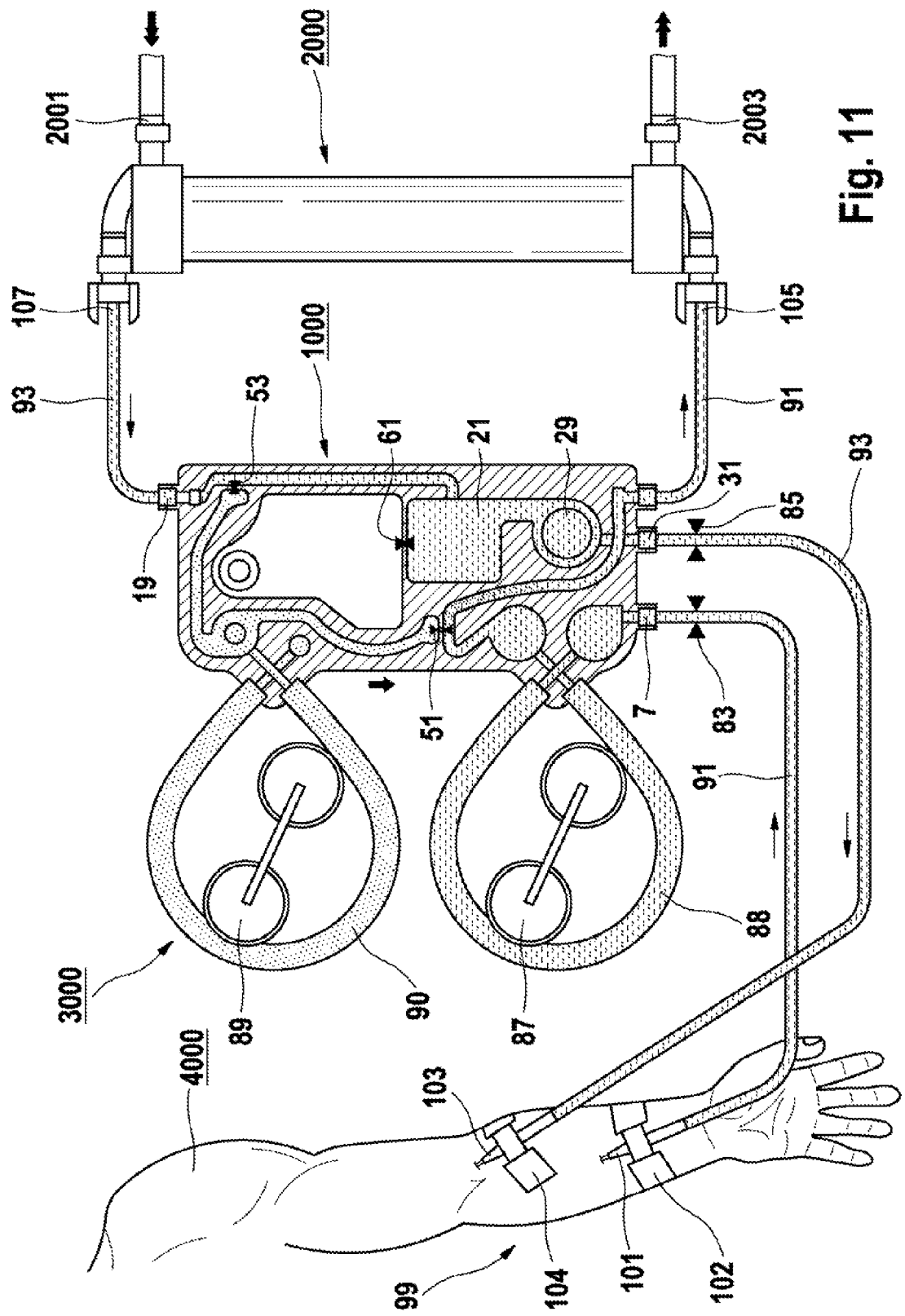
FIG. 11 shows in a simplified schematic representation a phase during the performance of the blood treatment process in accordance with the invention of FIG. 8 by using mixing dilution (pre-dilution).
Figure 12:
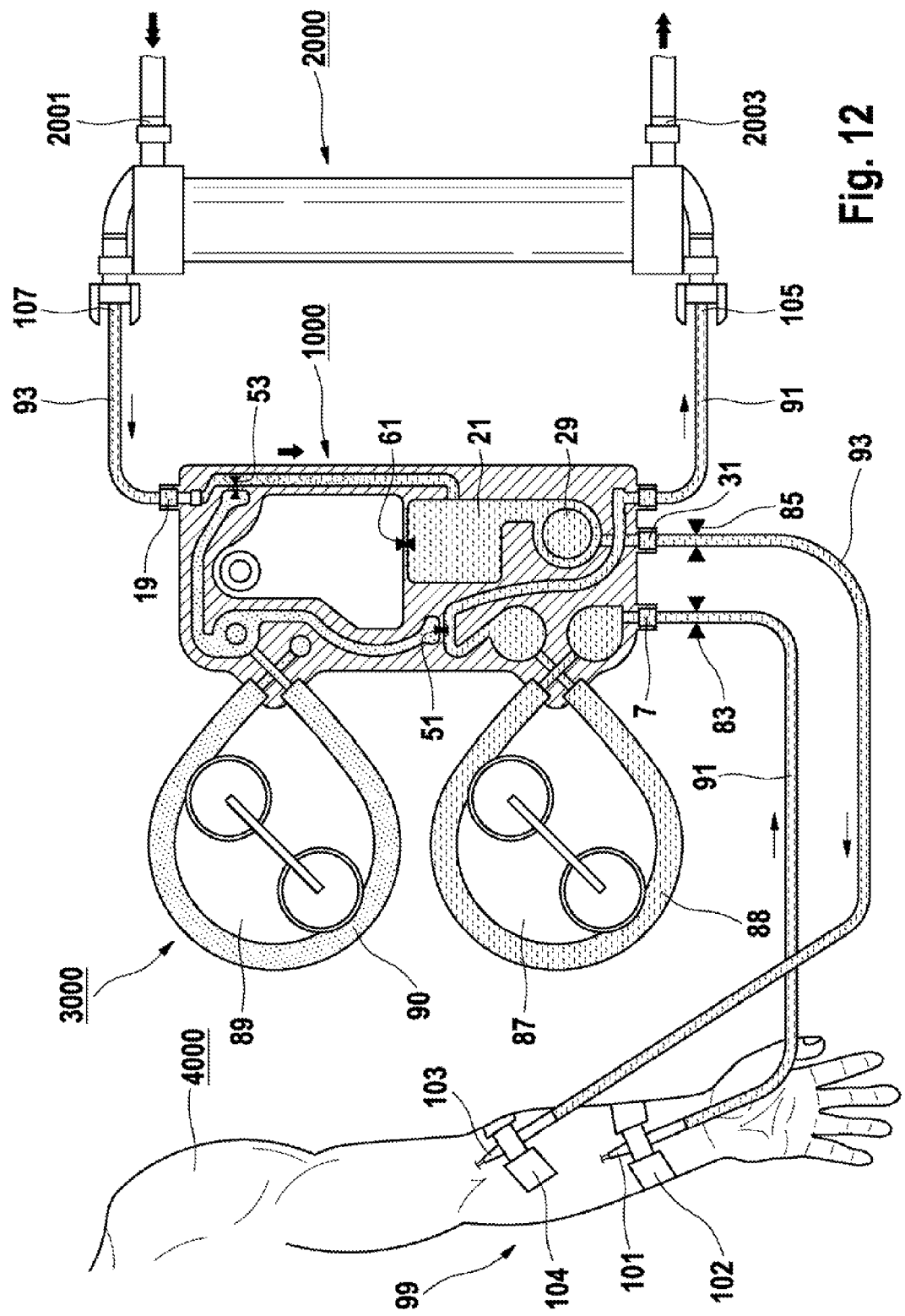
FIG. 12 shows in a simplified schematic representation a phase during the performance of the blood treatment process in accordance with the invention of FIG. 8 by using mixing dilution (post-dilution).

FIG. 11 and FIG. 12 show phases of the blood treatment process represented in FIG. 8 by using a mixing dilution of the blood with substitute ("on-line HDF mixing dilution—switched"). The expression "mixing dilution" designates diluting of the blood with substitute that alternatingly takes place via pre-dilution or post-dilution.

FIG. 11 illustrates the pre-dilution interval of the mixing dilution in a momentary state;

FIG. 12 illustrates the post-dilution interval of the mixing dilution in a momentary state.

The process shown with the aid of FIG. 11 corresponds to the one of the process shown with the aid of FIG. 9; the process shown with the aid of FIG. 12 corresponds to the one of FIG. 10. The blood pump 87 and the substituate pump 89 rotate in synchronicity. The blood pump 87 and the substituate pump 89 may, for example, rotate faster than in the processes or process stages represented in FIGS. 9 and 10.

Figure 13:
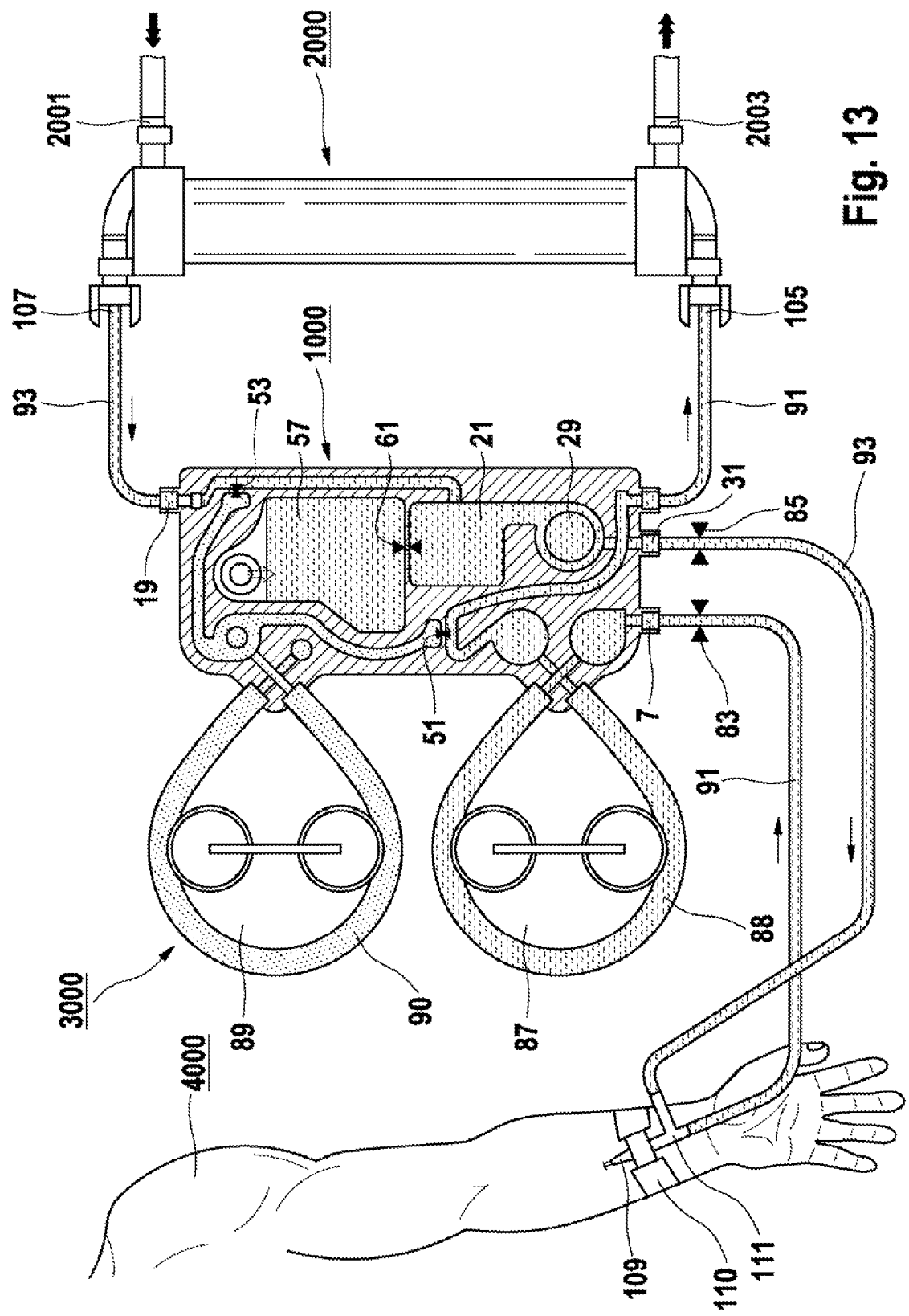
FIG. 13 shows in a simplified schematic representation a phase during the performance of a second blood treatment process in accordance with the invention by using a single-needle access.

FIG. 13 shows the cassette 1000 and the extracorporeal circuit 3000 in a phase of a dialysis treatment by means of a single-needle access to the patient ("Cassette Integrated Single Needle").

A single-needle access 109 was placed on the patient 4000 and fixed by means of a fixation 110. A fixation 110 may, for example, in turn be realized as a sleeve, a tape, or the like.

The single-needle access 109 comprises a Y-piece or a Y-shaped branching 111 into the arterial portion 91 and the venous portion 93 of the extracorporeal circuit 3000.

The arterial patient tube clamp 83 is opened. The venous patient tube clamp 85 is initially closed. This is not represented in FIG. 13.

The blood pump 87 is started. The dialyzing means 2000 is operated. Blood from the patient 4000 is conveyed through the arterial portion 91 into the dialyzing means 2000. In the dialyzing means 2000 the blood is purified. The purified blood is introduced into the venous portion 93 of the extracorporeal circuit 3000.

The blood enters into the venous blood chamber 21 of the cassette 1000. The single-needle blood valve 61 is opened. Blood flows into the single-needle chamber 57.

When the single-needle chamber 57 is nearly filled, the blood pump 87 is stopped and the venous patient tube clamp 85 is opened, as may be seen in FIG. 13. The dialyzing process is stopped.

The blood is discharged by gravity from the cassette 1000, the single-needle chamber 57, the venous blood chamber 21 and the clot trap 29, and recirculated into the patient 4000.

When the single-needle chamber 29 is nearly emptied of blood, the blood pump 87 is started again.

This phase of the blood treatment is repeated as often as necessary.

Figure 14:
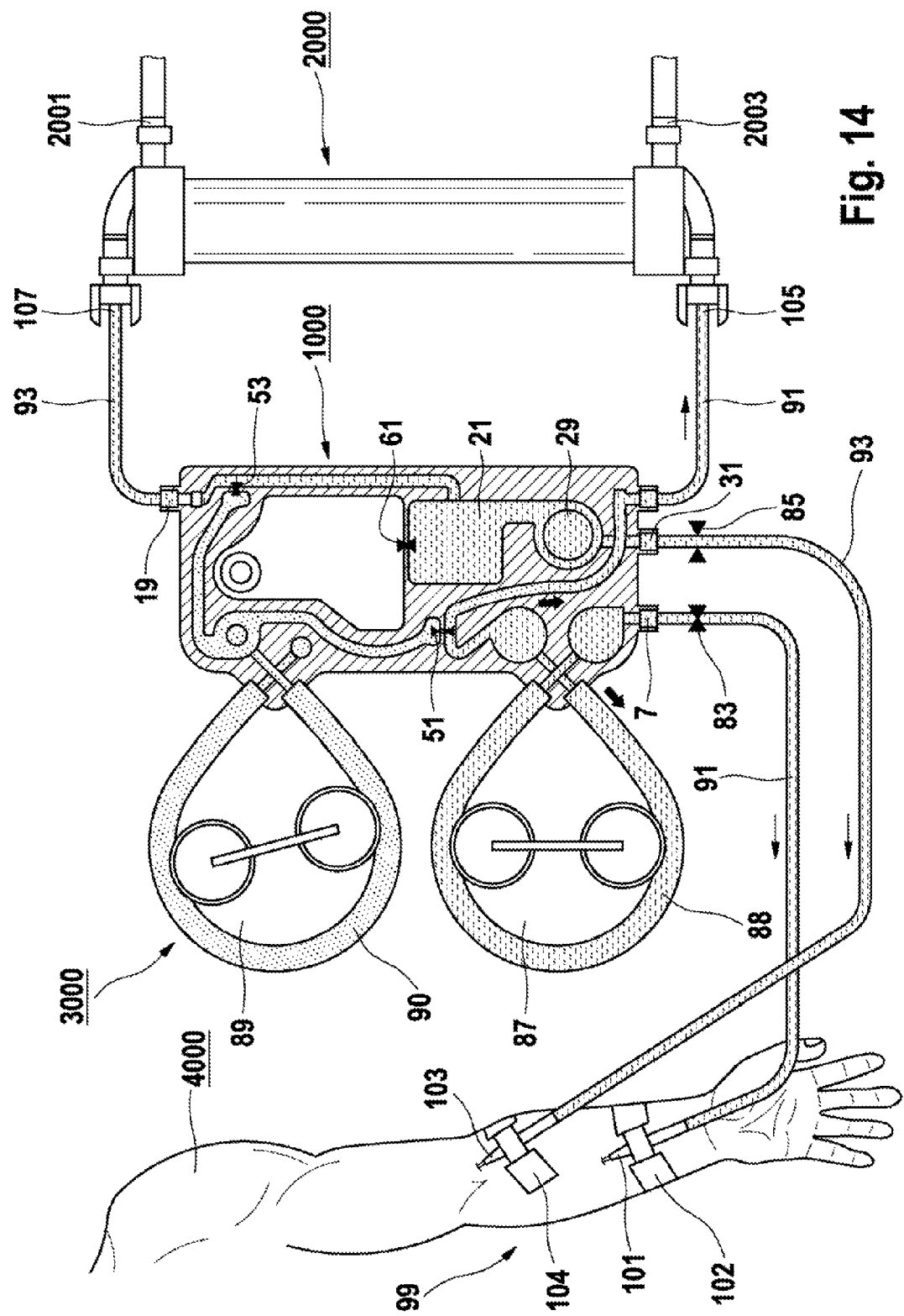
FIG. 14 shows in a simplified schematic representation a phase during the performance of a first blood recirculation process in accordance with the invention.

FIG. 14 shows a phase of a first variant of a blood recirculation process following termination of the blood treatment.

The arterial patient tube clamp 83 is opened. The venous patient tube clamp 85 is closed. The substituate pump 89 is operated.

Blood is present in the extracorporeal circuit 3000. Substituate is present in the substituate conduit 49.

The pre-dilution addition valve 51, the post-dilution addition valve 53, and the single-needle blood valve 61 are initially closed.

The pre-dilution addition valve 51 is opened. Substituate is conveyed through the arterial portion 91 of the extracorporeal circuit 3000 towards the dialyzing means 2000.

The blood which is present in the extracorporeal circuit 3000 behind or upstream from the pre-dilution addition valve 51 relative to the conveying direction is conveyed through the dialyzing means 2000 and the venous portion 93 to the patient 4000.

Shortly before the substituate reaches the venous needle 103, the substituate pump 89 is stopped.

The venous patient tube clamp 85 is opened. The arterial patient tube clamp 83 is closed.

FIG. 14 shows the configuration of the cassette 1000 in a momentary state during the process in which the substituate is introduced upstream through the opened pre-dilution addition valve 51 into the extracorporeal circuit 3000 to displace the blood.

The blood pump 87 and the substituate pump 89 are operated. The blood pump 87 rotates in the clockwise direction and thus against the conveying direction. The substituate pump rotates in the counter-clockwise direction. The blood pump 87 and the substituate pump 89 may rotate at an offset from each other.

The substituate is conveyed from the post-dilution addition valve 53 into the arterial portion 91 of the extracorporeal circuit 3000 and through the pump tube segment 88 of the blood pump 87 towards the patient 4000. The substituate displaces the blood which is present in the arterial portion 91 between the arterial needle 101 and the pre-dilution addition valve 51.

Shortly before the substituate reaches the arterial needle 101, the blood pump 87 and the substituate pump 89 are stopped.

Figure 15:
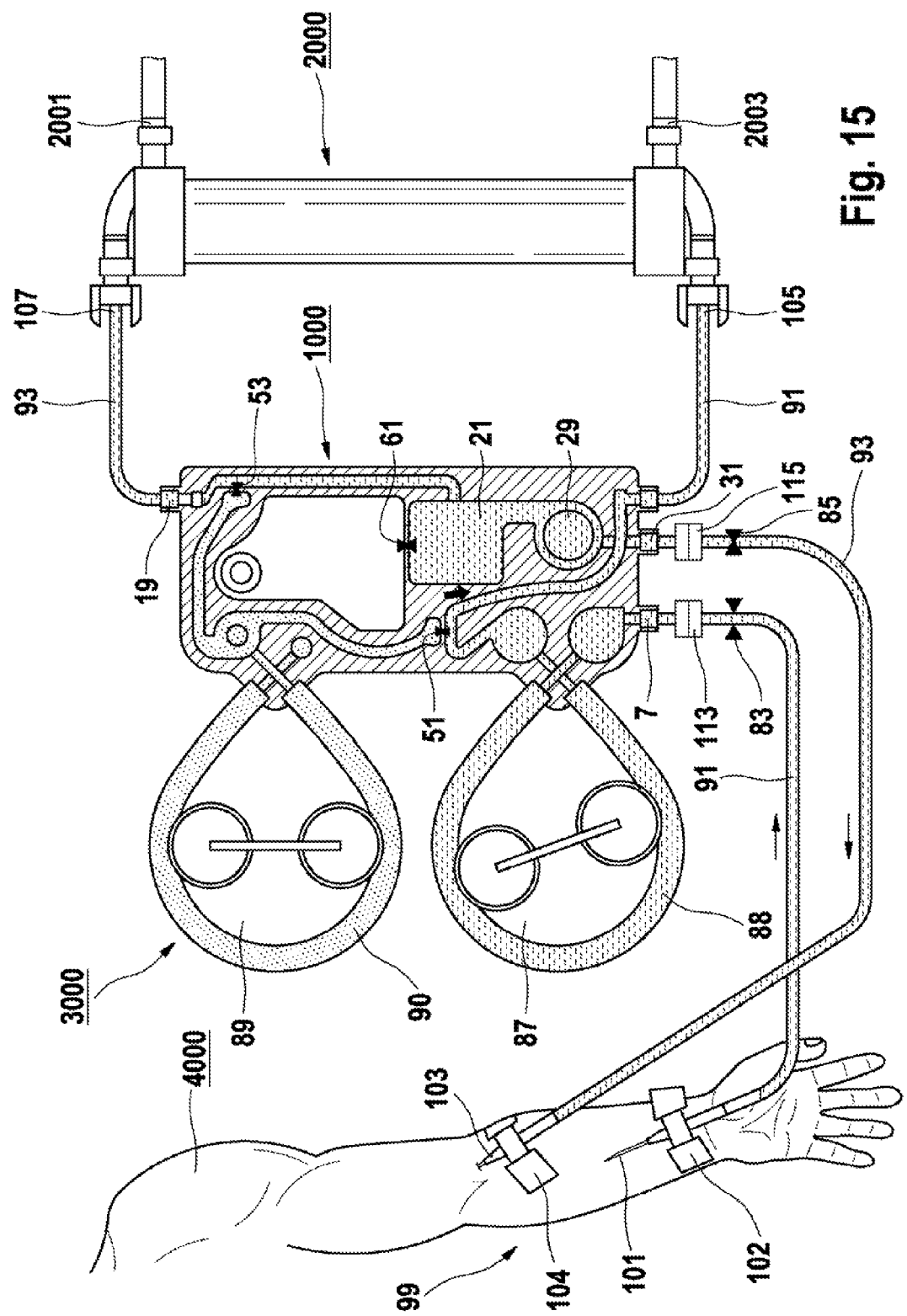
FIG. 15 shows in a simplified schematic representation a phase during the performance of a second blood recirculation process in accordance with the invention.

FIG. 15 illustrates a phase of an alternative blood recirculation process. At the arterial patient tube clamp 83 and the venous patient tube clamp 85 a respective sensor/detector 113 and sensor/detector 115 for measuring the optical density of the conduit interior of the extracorporeal circuit 3000 and for automatic recognition of the appearance of substituate are provided. Other and/or additional suitable sensors may be employed. Sensor and detector may be realized as a single-component part or as separate components.

The fixation 102 of the arterial needle 101 is released and the arterial needle 101 is withdrawn. The arterial patient tube clamp 83 is opened. The pre-dilution addition valve 51 is closed.

The venous needle 103 remains connected to the patient 4000. The venous patient tube clamp 85 is closed.

The blood pump 87 is operated in the conveying direction and conveys blood out of the arterial portion 91 of the extracorporeal circuit 3000.

In FIG. 15, a corresponding momentary state of the process showing a condition shortly after the beginning of the process is shown.

The sensor/detector 113 recognizes the appearance of substituate. The blood is conveyed until it reaches the pre-dilution addition valve 51. Then the blood pump 87 is stopped.

The substituate pump 89 is started. The arterial patient tube clamp 83 is closed. The venous patient tube clamp 85 is opened.

The pre-dilution addition valve 51 is opened. The substituate pump 89 conveys the substituate through the arterial portion 91 of the extracorporeal circuit 3000, through the dialyzing means 2000 and the venous portion 93 of the extracorporeal circuit 3000, until the sensor/detector 115 at the venous patient tube clamp 85 recognizes the appearance of substituate.

The blood is conveyed back through the venous needle 103 to the patient 4000.

Figure 16:
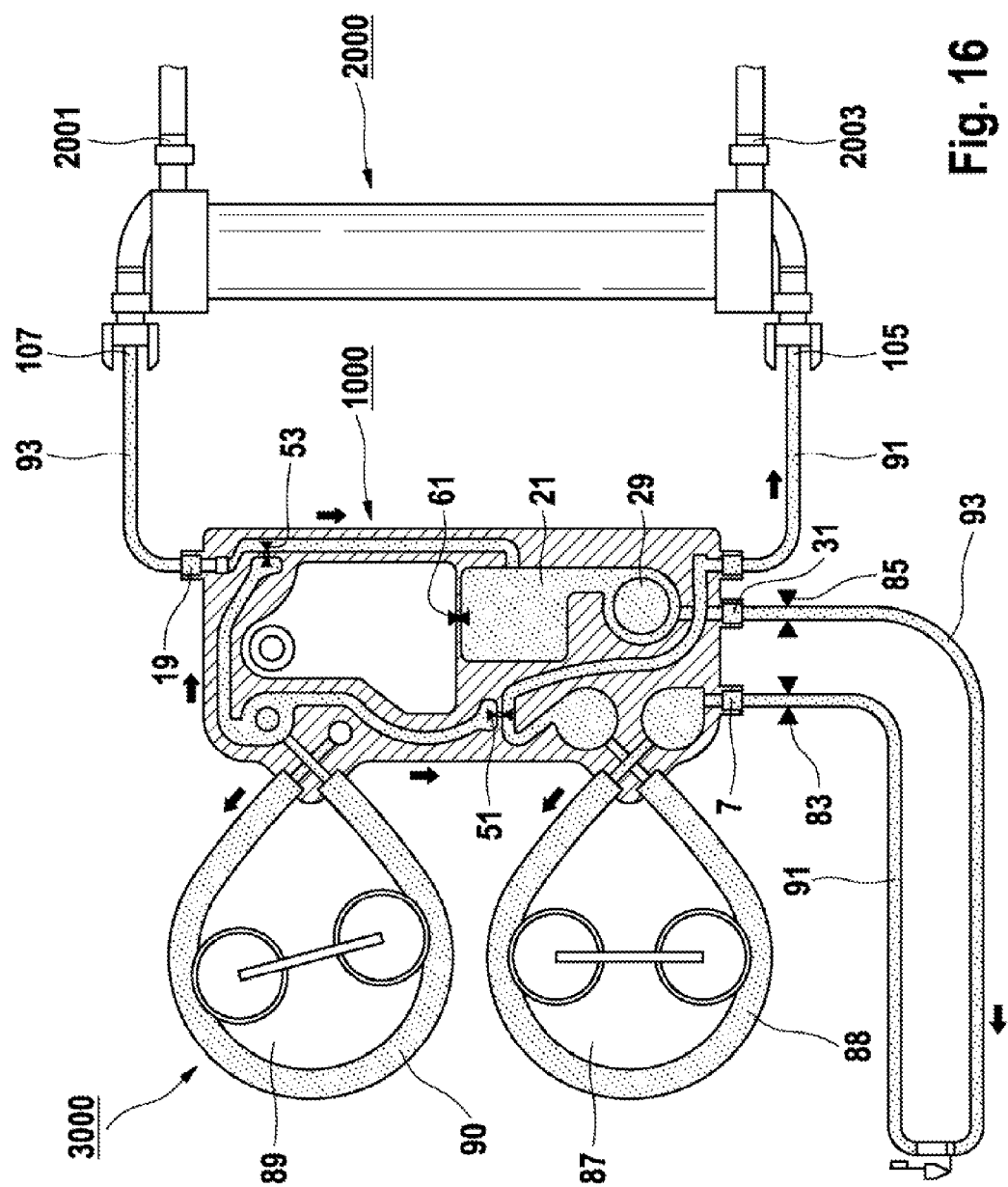
FIG. 16 shows in a simplified schematic representation a phase during the performance of an emptying process in accordance with the invention following the performance of a blood treatment process.

FIG. 16 shows the cassette 1000 and the extracorporeal circuit 3000 in a phase of an emptying process.

The patient is not connected to the treatment apparatus any more. The arterial portion 91 and the venous portion 93 of the extracorporeal circuit 3000 are connected to each other.

The arterial patient tube clamp 83 and the venous patient tube clamp 85 are opened. The pre-dilution addition valve 51 and the post-dilution addition valve 53 are opened, as is illustrated in FIG. 16 in the form of a momentary state.

Air is introduced through the substituate addition site 41 into the extracorporeal circuit 3000 by operating the substituate pump 89. The air flows through the opened pre-dilution addition valve 51 and the opened post-dilution addition valve 53 and thus enters the extracorporeal circuit 3000.

The air flows through the extracorporeal circuit 3000 and the dialyzing means 2000 in the opposite direction.

The pre-dilution addition valve 51 is closed and the blood pump 87 is operated. The blood pump 87 and the substituate pump 89 convey the air in the conveying direction through the cassette 1000 into the dialyzing means 2000. The air exits at the dialyzing liquid outlet 2003.

Further suitable methods for recirculation of the blood into a patient and/or for emptying the extracorporeal circuit are described, for example, in German Patent Application No. 10 2009 008 346.4 having the title "Verfahren zum Entfernen von Blut aus einem extrakorporalen Blutkreislauf for eine Behandlungsvorrichtung nach Beenden einer Blutbehandlungssitzung and Vorrichtung zum Ausführen desselben" [Method of removing blood from an extracorporeal blood circuit for a treatment apparatus following termination of a blood treatment session, and apparatus for performing said method] that was filed with the German Patent and Trademark Office on Feb. 11, 2009, the relevant disclosure of which is herewith fully incorporated by way of reference thereto.

Such methods are moreover described in German Patent Application No. 10 2009 024 606.1 to the present applicant having the title "Verfahren zum Entfernen von Blut aus einem extrakorporalen Blutkreislauf, Behandlungsvorrichtung sowie Schlauchsystem" [Method of removing blood from an extracorporeal blood circuit, treatment apparatus, and tubing system] as filed with the German Patent and Trademark Office on Jun. 10, 2009. The relevant disclosure thereof is herewith also fully incorporated into the present application by way of reference.

FIG. 17 shows in a simplified schematic representation an external functional means 1000 according to the invention according to a further embodiment in a view on its front side. With respect to the predominant number of its features, the cassette 1000 shown in FIG. 17 as well as in all other of the following figures corresponds to the embodiment of the cassette 1000 shown in FIGS. 1 to 16.

The embodiment of the cassette 1000 shown in FIG. 17 comprises a handhold 117 for—advantageously simply and/or rapidly—assembling and/or disassembling the cassette 1000 prior to or after termination of the blood treatment. The handhold 117 can also be of use in a disassembling generally requiring more effort.

The handhold can be designed such as to be actuated by means of tools, i.e., not to be actuated primarily or exclusively manually.

Furthermore, the embodiment of the cassette 1000 shown in FIG. 17 comprises an extraction point or fill post 119, respectively. The fill post 119 of the cassette 1000 can be provided for extracting or sampling, respectively, substituate from the cassette 1000.

The fill post 119 can be provided in addition to all structures and lines shown in FIGS. 1 to 16.

The fill post 119 can be provided for not being flushed by fluid during the normal blood treatment operation of the cassette 1000. Preferably, in such a case, no fluid leaves the cassette 1000 through the fill post 119 or enters the cassette 1000 through the fill post 119 during the treatment.

According to the invention, the fill post 119 can also be provided at another position than the position shown in the figures.

According to the invention, the fill post 119 can, for example, in exceptional cases serve as a site or position, respectively, for extracting or removing, respectively, a fluid such as, e.g., substituate. The extracted fluid, e.g., substituate, can be used as displacing fluid upon optionally manually returning or an arterial infusion of extracorporeal blood into the vascular system of the patient through the arterial line. The latter can be of use in the case of a blockage of certain lines or in the case of a failure of cassette functions or of functions of the treatment apparatus, in that, by means of the fill post, a fluid suited for returning can be obtained with little effort.

The fill post 119 can be provided at and connected with the cassette 1000 in different ways. In certain embodiments according to the invention, the fill post is integrally produced with the housing body of the cassette 1000. The fill post can be or comprise a Luer locking device injected onto the cassette.

In some embodiments according to the invention, the fill post comprises a valve, in particular a switchable valve.

In certain embodiments according to the invention, the fill post is also suited and provided for adding a fluid into the substituate.

The external functional means 1000 of FIG. 17 further comprises tube fixations 121 and 123. The tube fixations 121, 123 which may also be provided in any number different from two can in certain embodiments advantageously prevent a disruption or damage of the tubes required for using the cassette during handling of the cassette 1000 by, for example, hanging in, e.g., the door opening of the treatment apparatus during coupling of the cassette 1000.

Reference numeral 125 denotes a non-return valve or check valce which is, for example, designed such as is disclosed in German Patent Application No. 10 2009 024 469.7 to the applicant of the present invention having the title "Ventilvorrichtung, Ventileinsatz, externe Funktionseinrichtung, Behandlungsvorrichtung sowie Verfahren" [Valve device, valve insert, external functional means, treatment apparatus, and method] as filed with the German Patent and Trademark Office on Jun. 10, 2009, and U.S. Provisional Patent Application No. 61/185,603, also filed on Jun. 10, 2009.

The non-return valve 125 can be an addition valve of a venous line.

FIG. 17 furthermore discloses a heparin addition site 127. In the exemplary embodiment of FIG. 17, it is arranged in an upper area of the cassette 1000 above the single needle chamber 57 and above the venous blood chamber 21.

The heparin addition site 127 is in fluid communication with a supplying line for heparin, shortly termed heparin line 128. In the embodiment of FIG. 17, the heparin line 128 extends from the heparin addition site 127 downwards until it reaches a level of the cassette 1000 where the venous blood chamber 21 begins.

Furthermore, FIG. 17 reveals that the cassette 1000 comprises comparably less function exerting structures in a lower border area U, e.g., in the vicinity of clot trap 29 or beneath. This provides for space in the border area U of the cassette 1000 enabling the coupling of the cassette 1000 with measurement devices or the like which are, e.g., connected with the treatment apparatus, a door thereof or other devices or means, respectively. Such measurement devices can be arterial and/or venous temperature sensors, air bubble detectors, sensors for measuring an optical density, and the like.

Providing space required therefore and the resulting possibility of providing the space with the afore-mentioned or other sensors thus contributes to process safety and thereby reduces or excludes risks for the patient.

It should be clear that the space U may also be provided in another part or section, respectively, of the cassette 1000. Likewise, more than one of such spaces may be provided. Preferably such spaces are provided in a border or rim or edge area of the cassette 1000 and/or at or in the vicinity or proximity of supplying or discharging lines. Due to such favorable positions of possible sensors, the space directly or indirectly also serves for increasing the accessibility, for improving ergonomic aspects as well as for reducing costs, e.g., for connecting or coupling, respectively, the aforementioned sensors with analyzing devices (short signal lines).

FIG. 18 shows in a schematic simplified manner an enlarged representation of a section A of FIG. 17. The non-return valve 125 shown in FIG. 18 in an enlarged representation can, e.g., be integrated in the cassette 1000 as a valve for post dilution addition of substituate such that it can be flushed by substituate after termination of the treatment. In this way, by using this arrangement, it can advantageously be possible to vent cavities during priming and rinsing the cassette 1000 in the proximity of the non-return valve in a more efficient way. It can advantageously be possible to avoid remaining of visible blood residues after having emptied the cassette 1000 after termination of the blood treatment. So, this can optionally contribute to a reduction of the contamination risk for third parties upon disposing the cassette 1000 after its use in case of blood residues. The non-return valve 125 is preferably arranged such as to be flushed without human assistance in particular during conventional use of the cassette 1000.

Further, FIG. 18 shows a phantom valve 129 as well as a phantom valve 130. Phantom valves are specified in other sections of the application. For details, it is referred to these sections.

FIG. 19 shows in a schematically simplified representation the external functional means according to the invention of the further embodiment represented in a slightly perspective view substantially from its back side.

Besides the structures which have already been discussed above with respect to the other figures, the embodiment of the cassette 1000 shown in FIG. 19 further comprises an addition site 131 comprising a septum. The addition site 131 comprising the septum (also shortly termed septum addition site) is arranged at the level of the upper border or edge, respectively, of the cassette 1000 in the embodiment shown in FIG. 19. The upper border of FIG. 19 is one example of an upper area of the cassette 1000.

FIG. 20 shows in a schematically simplified representation section B of the representation of FIG. 19 in an enlarged view.

FIG. 21 shows in a schematically simplified representation the external functional means according to the invention in a further embodiment in a slightly perspective view, substantially viewed from its front side.

Other than in the embodiment of, e.g., FIG. 17, the cassette 1000 does not comprise a fill post (denoted with reference numeral 119 there) in this further embodiment.

FIG. 22 shows in a schematically simplified representation section A of the representation of FIG. 21 in an enlarged view. An arrangement of the phantom valve differing from the arrangement of FIG. 18 can well be identified. The different arrangement may result in different flushability.

FIG. 23 shows in a schematically simplified representation further details, i.e. of section B, of the representation of FIG. 21.

As can be seen from FIG. 23, the venous blood chamber 21 comprises an indentation 133 or contraction or an inclination modification or diminution or asymmetry of the inner and/or outer wall of the venous blood chamber 21. Both in FIG. 21 and in FIG. 23, the indentation 133 is shown at the right border and at the front side of the venous blood chamber 21.

The indentation 133 can at least be present at the side facing the supplying line.

The indentation 133 can be present in a section of the periphery or at the entire periphery of the rigid part of the venous chamber.

In a position of use of the blood cassette 1000, the indentation 133 can be arranged substantially horizontally.

In certain embodiments, the indentation 133 can correspond to or comprise a modification of the periphery and/or of the diameter of a section of the venous blood chamber 21 or of a wall thereof.

In some embodiments according to the invention, with respect to a horizontal section (in relation to the representation of the cassette 1000 in FIG. 21 or of the arrangement of the cassette 1000 during its use), the indentation 133 can be or can comprise a non-semi-circular diameter of the venous blood chamber 21 (at the level of the indentation 133).

In certain embodiments according to the invention, the indentation 133 can be a diminution of the cross-section of the chamber, in particular in the top to bottom direction of the representation of FIG. 21.

In some embodiments according to the invention, the indentation 133 can be a section or an transition zone in or by which a larger cross-section or a larger cross-section area of the venous blood chamber 21 passes over to a smaller cross-section or a smaller cross-section area of the venous blood chamber 21, in particular in the top to bottom direction of the representation of FIG. 21.

In certain embodiments according to the invention, the indentation 133 can be a dent extending along a section of the periphery of the venous blood chamber 21, in particular in the top to bottom direction of the representation of FIG. 21.

In certain embodiments, the indentation 133 can result in an asymmetrical form of the venous blood chamber 21 in relation to the representation of FIG. 21 in the top to bottom direction.

The indentation 133 which can partly or completely extend along the entire cross-section of the venous blood chamber 21 has surprisingly resulted in a reduced frothing or foam formation, respectively, within the venous blood chamber 21.

With the optimization of the geometry of the venous blood chamber 21 achieved by means of the indentation 133 by which optionally the geometry of a single needle valve could also have been optimized, in certain embodiments of the present invention, an improved venting may be achieved prior to the beginning of the treatment. Furthermore, in some embodiments according to the invention, an improved steam flow during sterilization can be achieved. Moreover, in certain embodiments according to the invention, a reduction of eddy water spaces or areas comprising the known advantages resulting therefrom may be achieved.

FIG. 24 shows in a schematically simplified representation the external functional means according to the invention in form of a cassette 1000 in a perspective, viewed from the bottom side and from the front side.

FIG. 25 shows in a schematically simplified representation the section C of the representation of FIG. 24 in an enlarged view. It can be seen that a valve seating 135 of the single needle (SN) valve is lowered when compared to the proximity or adjacent bars or parts of the housing body of the cassette 1000. Hereby, the inventors could achieve fluidic advantages which could come along not only with avoiding or reducing the formation of turbulences. The lowering can be, e.g., 0.5 mm.

FIG. 26 shows in a schematically simplified representation the section D of the representation of FIG. 24 in an enlarged view. It can be seen from FIG. 26 that valve seatings 137 and 139 of phantom valves are lowered against the proximity or adjacent bars or parts of the housing body of the cassette 1000. The lowering can be, e.g., 0.5 mm.

The following is a List of Reference Numerals as used herein.

| Reference Numeral | Description |
|---|---|
| 1000 | cassette |
| 1 | hard part |
| 3 | film |
| 4 | sealing bar |
| 5 | peripheral weld |
| 7 | arterial patient connection |
| 9 | arterial pressure measurement chamber |
| 11 | connector for the exit of blood from cassette 1000 |
| 13 | connector for the entry of blood into cassette 1000 |
| 15 | chamber with arterial post-pump, or pre-filter, pressure measurement site |
| 17 | arterial filter conduit |
| 19 | venous filter conduit |
| 21 | venous blood chamber |
| 23 | upper space of the venous blood chamber 21 |
| 25 | lower space of the venous blood chamber 21 |
| 27 | cross-sectional restriction of the hard part 1 |
| 29 | clot trap |
| 31 | venous patient connection |
| 33 | arterial addition site |
| 35 | check valve of the arterial addition site 33 |
| 36 | arterial heparin addition valve (phantom valve) |
| 37 | venous addition site |
| 39 | check valve of the venous addition site 37 |
| 40 | venous heparin addition valve (phantom valve) |
| 41 | substituate addition site |
| 43 | connector for exit of substituate from the cassette 1000 |
| 45 | connector 45 for entry of substituate into the cassette 1000 |
| 47 | check valve for addition of substituate |
| 49 | substituate conduit |
| 51 | pre-dilution addition valve (phantom valve) |
| 53 | post-dilution addition valve (phantom valve) |
| 55 | single-needle sterile membrane |
| 57 | single-needle chamber |
| 59 | blood surge redirection element |
| 61 | single-needle blood valve (phantom valve) |
| 63 | evacuation site for vacuum coupling |
| 65 | primary alignment center |
| 67 | secondary alignment site |
| 69 | sealing bar |
| 71 | single-needle air connector |
| 73 | support bars having a height of 5 mm |
| 75 | support bars having a height of 8 mm |
| 77 | support bars having a height of 13 mm |
| 79 | support bars having a height of 24 mm |
| 81 | support bars having a height of 31 mm |
| 2000 | dialyzing means |
| 2001 | dialyzing liquid inlet |
| 2003 | dialyzing liquid outlet |
| 3000 | extracorporeal circuit |
| 83 | arterial patient tube clamp |
| 85 | venous patient tube clamp |
| 87 | blood pump |
| 88 | pump tube segment of blood pump 87 |
| 89 | substituate pump |
| 90 | pump tube segment of substituate pump 89 |
| 91 | arterial portion of extracorporeal circuit 3000 |
| 93 | venous portion of extracorporeal circuit 3000 |
| 95 | drain conduit |
| 97 | plug valve |
| 4000 | patient |
| 99 | double-needle access to patient 4000 |
| 101 | arterial needle |
| 102 | fixation of arterial needle |
| 103 | venous needle |
| 104 | fixation of venous needle |
| 105 | blood inlet at the dialyzing means 2000 |
| 107 | blood outlet from the dialyzing means 2000 |
| 109 | single-needle access to patient 4000 |
| 110 | fixation of single-needle access 109 |
| 111 | Y-shaped branching of the single-needle access 109 into arterial portion 91 and venous portion 93 |
| 113 | sensor/detector at arterial patient tube clamp 83 |
| 115 | sensor/detector at venous patient tube clamp 85 |
| 117 | handhold |
| 119 | fill post |
| 121 | tube fixation |
| 123 | |
| 125 | non-return valve |
| 127 | heparin addition site |
| 128 | heparin line |
| 129 | phantom valve |
| 130 | |
| 131 | addition site |
| 133 | indentation |
| 135 | valve seating |
| 137 | |
| 139 | |

What is claimed is:

1. A medical device, comprising:
at least one housing body,
at least one chamber integrated into the housing body for receiving medical fluids;
at least one passage integrated into the housing body for at least one of receiving and conducting a medical fluid;
at least one valve completely or partly integrated into the housing body for controlling or regulating a fluid flowing through the medical device; and
at least one venous blood chamber;
wherein the medical device is a cassette configured for a blood treatment by dialysis having at least one single-needle chamber for a single-needle access to a patient;
wherein the single-needle chamber is disposed on a venous blood side of the medical device and above the venous blood chamber relative to an orientation of the medical device during its use, the single-needle chamber being in fluid communication with the at least one passage integrated into the housing body for at least one of receiving and conducting a medical fluid only via the venous blood chamber.

2. The medical device according to claim 1, further comprising at least one surface on which a cover is provided, the cover being part of the at least one integrated valve.

3. The medical device according to claim 2, wherein the cover is connected by at least one of friction, form closure, and material connection to the housing body in at least one portion thereof.

4. The medical device according to claim 3, wherein the cover is connected to the housing body by at least one peripheral weld.

5. The medical device according to claim 3, wherein the cover is additionally connected to the housing body by non-peripheral or dot-shaped or local welds.

6. The medical device according to claim 3, wherein the cover is connected at two sides or bilaterally with at least one structure of the medical device.

7. The medical device according to claim 6, wherein the at least one structure is the at least one housing body.

8. The medical device according to claim 2, wherein the cover is a film.

9. The medical device according to claim 1, further comprising connections configured to connect the medical device to an extracorporeal circuit in fluid communication.

10. The medical device according to claim 9, further comprising at least one addition site including at least one septum and configured to supply a fluid which is not blood or not exclusively blood, into an interior or into a line section of the medical device.

11. The medical device according to claim 9, wherein the blood treatment cassette comprises, in a portion of an extracorporeal circuit contained in the blood treatment cassette, at least one arterial cassette-integrated chamber and at least one venous cassette-integrated chamber, wherein the cassette comprises at least one film as a cover, and wherein at least one of an arterial and a venous pressure present in the extracorporeal blood circuit is measurable through the intermediary of the film.

12. The medical device according to claim 11, further comprising a sensor configured to measure at least one of the arterial and venous pressure above at least one of the arterial and venous chamber through the intermediary of the film.

13. The medical device according to claim 1, further comprising a supplying line for an anticoagulant, the supplying line being completely or partly arranged in an upper area with respect to an alignment of the medical device during use, or in a border area of the medical device.

14. The medical device according to claim 1, further comprising at least one heparin line arranged at least in an area of the medical device that, during use of the medical device, is arranged in an upper area of the medical device.

15. The medical device according to claim 1, further comprising at least one handle bar or handhold for at least one of connecting and separating the medical device with or from a treatment apparatus.

16. The medical device according to claim 1, further comprising at least one fill post configured to extract a fluid which is not blood, or not exclusively blood, from the medical device while the medical device is connected with a treatment apparatus for the purpose of its use.

17. The medical device according to claim 1, further comprising at least one tube fixation configured to fix at least one section of at least one tube at the medical device while the medical device is coupled to a treatment apparatus.

18. The medical device according to claim 1, wherein the medical device is adapted to be connected in fluid communication to at least one peristaltic pump by two connectors.

19. The medical device according to claim 18, wherein the peristaltic pump is a roller pump.

20. The medical device according to claim 18, further comprising at least one pump tube segment.

21. The medical device according to claim 1, further comprising at least one valve having a) at least one bar formed on the housing body and b) at least one portion of the cover, wherein the at least one bar and the at least one portion of the cover are operable by an actor of a blood treatment apparatus acting on the at least one bar via the cover in order to alter a passage of fluid.

22. The medical device according to claim 1, wherein the fluid includes at least one of a) substituate, b) heparin, c) blood, d) saline solution, and e) air.

23. The medical device according to claim 1, wherein the medical device is adapted to be coupled to a blood treatment apparatus.

24. The medical device according to claim 23, wherein the medical device is configured to be coupled to the blood treatment apparatus via a reception means.

25. The medical device according to claim 23, wherein the medical device is adapted to be coupled to the blood treatment apparatus at an inclination angle of substantially or precisely 8 degrees relative to a vertical.

26. The medical device according to claim 23, wherein the medical device is adapted to be coupled to the treatment apparatus at a surface of the medical device facing the cover.

27. The medical device according to claim 1, comprising at least one substituate addition site having at least one of a) touch-protection element and b) a drip-protection element.

28. The medical device according to claim 27, wherein the drip-protection element is provided as an integrated closure sleeve.

29. The medical device according to claim 1, wherein the medical device is configured to perform a blood treatment using a double-needle access to a patient.

30. The medical device according to claim 1, wherein the at least one single-needle chamber includes a blood surge redirection element.

31. The medical device according to claim 1, wherein the venous blood chamber is subdivided into at least one upper space and at least one lower space by a cross-sectional restriction of the housing body.

32. The medical device according to claim 31, wherein the upper space and the lower space are in fluid communication or connection with each other, and the upper space is configured to admit or generate a tangential inflow of fluids flowing through the medical device.

33. The medical device according to claim 31, wherein the upper space includes a region for generating a stable rotational flow of the fluids flowing through the medical device.

34. The medical device according to claim 33, wherein the lower space includes a region that is substantially or entirely free from rotational flow of the fluids flowing through the medical device.

35. The medical device according to claim 31, wherein walls of at least one of the upper space and the lower space of the venous blood chamber are adapted to an inclination of the medical device against a vertical of the blood treatment apparatus.

36. The medical device according to claim 1, wherein at least one wall of the venous blood chamber comprises at least one indentation.

37. The medical device according to claim 1, wherein the housing body is configured as a hard part.

38. The medical device according to claim 1, further comprising a tamper protection.

39. The medical device according to claim 38, wherein the tamper protection is provided via a configuration of a substituate addition site.

40. The medical device according to claim 38, wherein the tamper protection is provided via a touch-protection element or a closure sleeve of a substituate addition site, at least one of based on a change of the position of the touch-protection element or closure sleeve within or relative to the cassette and based on a change of the shape of the touch-protection element or closure sleeve.

41. The medical device according to claim 1, further comprising a protection against reuse.

42. The medical device according to claim 41, wherein the protection against reuse is via a configuration of the substituate addition site.

43. The medical device according to claim 41, wherein a closure sleeve is made unusable for reuse.

44. A blood treatment apparatus, comprising:
a dialysis apparatus wherein the blood treatment apparatus is in receipt of at least one medical device according to claim 1.

45. The blood treatment apparatus according to claim 44, further comprising at least one of at least one a) control means b) actor, and c) sensor, configured to at least one of drive and operate the medical device.

46. The blood treatment apparatus according to claim 44, further comprising at least one reception means for receiving the medical device.

47. The blood treatment apparatus according to claim 46, wherein the reception means comprises a coupling surface for coupling the medical device.

48. The blood treatment apparatus according to claim 47, wherein the coupling surface is inclined by an angle against a vertical relative to the orientation of the blood treatment apparatus during its use or to the center of the Earth.

49. The blood treatment apparatus according to claim 48, wherein the angle is between 5 and 11 degrees.

50. The blood treatment apparatus according to claim 48, wherein the angle is substantially or precisely 8 degrees.

51. A method, compising:
treating the blood of a patient using the medical device of claim 1.

52. The method according to claim 51, wherein the blood is treated using a double-needle method.

53. The method according to claim 51, wherein the blood is treated using a single-needle method.

54. The method of claim 51, further comprising:
conducting blood through a dialyzing filter to dialyze the blood; and
storing the blood that has passed through the dialyzing filter in a single-needle chamber of the medical device, wherein the blood is dialyzed in the dialyzing filter before entering into the single-needle chamber.

55. The method according to claim 51, further comprising:
inserting the medical device in a blood treatment apparatus; and
using sensors of the blood treatment apparatus to examine whether the medical device inserted in the blood treatment apparatus has already been used.

56. A method, comprising:
dialyzing blood using a double-needle procedure, wherein the dialyzing includes a pre-dilution;
during the dialyzing, operating the medical device according to claim 1.

57. A method, comprising:
dialyzing blood using a double-needle procedure, wherein the dialyzing includes a post-dilution; and
during the dialyzing, operating the medical device according to claim 1.

58. A method, comprising:
dialyzing blood using a double-needle procedure, wherein the dialyzing includes at least one pre-dilution step and at least one post-dilution step; and
during the dialyzing, operating the medical device according to claims 1.

59. A method, comprising:
dialyzing blood using a single-needle procedure; and
during the dialyzing, operating the medical device according to claim 1.

60. A dialysis apparatus, comprising:
the medical device according to claim 1, wherein the dialysis apparatus is configured to control the cassette.

* * * * *

UNITED STATES PATENT AND TRADEMARK OFFICE
CERTIFICATE OF CORRECTION

| | | |
|---|---|---|
| PATENT NO. | : 9,808,566 B2 | Page 1 of 1 |
| APPLICATION NO. | : 12/766424 | |
| DATED | : November 7, 2017 | |
| INVENTOR(S) | : Soeren Gronau et al. | |

It is certified that error appears in the above-identified patent and that said Letters Patent is hereby corrected as shown below:

In the Claims

Claim 51
Column 39, Line 28, delete "compising:" and insert --comprising:--.

Claim 58
Column 40, Line 28, delete "claims 1." and insert --claim 1.--.

Signed and Sealed this
Ninth Day of January, 2018

Joseph Matal
*Performing the Functions and Duties of the*
*Under Secretary of Commerce for Intellectual Property and*
*Director of the United States Patent and Trademark Office*